United States Patent
Itu et al.

(10) Patent No.: US 10,872,698 B2
(45) Date of Patent: Dec. 22, 2020

(54) METHOD AND SYSTEM FOR ENHANCING MEDICAL IMAGE-BASED BLOOD FLOW COMPUTATIONS USING PHYSIOLOGICAL MEASUREMENTS

(71) Applicant: Siemens Healthcare GmbH, Erlangen (DE)

(72) Inventors: Lucian Mihai Itu, Brasov (RO); Tiziano Passerini, Plainsboro, NJ (US); Puneet Sharma, Monmouth Junction, NJ (US); Thomas Redel, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 1012 days.

(21) Appl. No.: 15/221,180

(22) Filed: Jul. 27, 2016

(65) Prior Publication Data
US 2017/0032097 A1    Feb. 2, 2017

Related U.S. Application Data

(60) Provisional application No. 62/197,204, filed on Jul. 27, 2015.

(51) Int. Cl.
*G16H 50/50*    (2018.01)
(52) U.S. Cl.
CPC .................... *G16H 50/50* (2018.01)
(58) Field of Classification Search
CPC ............................................. G16H 50/50
USPC ............................................... 703/2
See application file for complete search history.

(56) References Cited

U.S. PATENT DOCUMENTS

| | | | |
|---|---|---|---|
| 6,236,878 B1 * | 5/2001 | Taylor | G16H 50/50 600/416 |
| 7,860,290 B2 | 12/2010 | Gulsun et al. | |
| 7,953,266 B2 | 5/2011 | Gulsun et al. | |
| 8,098,918 B2 * | 1/2012 | Zheng | G06T 7/62 382/131 |
| 8,157,742 B2 | 4/2012 | Taylor | |
| 8,200,466 B2 | 6/2012 | Spilker et al. | |
| 8,249,815 B2 | 8/2012 | Taylor | |
| 8,311,747 B2 | 11/2012 | Taylor | |
| 8,311,748 B2 | 11/2012 | Taylor et al. | |
| 8,311,750 B2 | 11/2012 | Taylor | |

(Continued)

OTHER PUBLICATIONS

C.A. Taylor, et al., "Open Problems in Computational Vascular Biomechanics: Hemodynamics and Arterial Wall Mechanics," Comput Methods Appl Mech. Eng., vol. 198, pp. 3514-3523, 2009.

(Continued)

*Primary Examiner* — Justin C Mikowski

(57) ABSTRACT

A method and system for simulating blood flow in a vessel of a patient to estimate hemodynamic quantities of interest using enhanced blood flow computations based on invasive physiological measurements of the patient is disclosed. Non-invasive patient data including medical image data is received and a patient-specific anatomical model the patient's vessels is generated. Invasive physiological measurements of the patient are received and a computational blood flow model is personalized using the invasive physiological measurements. Blood flow is simulated in the patient-specific anatomical model and one or more hemodynamic quantities of interest are computed using the personalized computational blood flow model.

48 Claims, 10 Drawing Sheets

(56) References Cited

U.S. PATENT DOCUMENTS

| | | |
|---|---|---|
| 8,315,812 B2 | 11/2012 | Taylor |
| 8,315,813 B2 | 11/2012 | Taylor et al. |
| 8,315,814 B2 | 11/2012 | Taylor et al. |
| 8,321,150 B2 | 11/2012 | Taylor |
| 8,386,188 B2 | 2/2013 | Taylor et al. |
| 2010/0017171 A1 | 1/2010 | Spilker et al. |
| 2010/0067760 A1 | 3/2010 | Zhang et al. |
| 2011/0224542 A1* | 9/2011 | Mittal ............... G06T 7/0016 600/425 |
| 2012/0022843 A1* | 1/2012 | Ionasec ............... G06T 13/20 703/9 |
| 2012/0041301 A1 | 2/2012 | Redel |
| 2012/0041318 A1* | 2/2012 | Taylor ............... A61B 5/02007 600/504 |
| 2012/0041319 A1 | 2/2012 | Taylor |
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053918 A1* | 3/2012 | Taylor ............... A61B 5/02007 703/9 |
| 2012/0053919 A1 | 3/2012 | Taylor |
| 2012/0053921 A1 | 3/2012 | Taylor |
| 2012/0059246 A1 | 3/2012 | Taylor |
| 2012/0072190 A1* | 3/2012 | Sharma ............... G06T 7/0016 703/2 |
| 2012/0121151 A1* | 5/2012 | Bernhardt ............... A61B 6/03 382/131 |
| 2012/0150516 A1 | 6/2012 | Taylor et al. |
| 2012/0203530 A1 | 8/2012 | Sharma et al. |
| 2012/0243761 A1* | 9/2012 | Senzig ............... G06T 11/008 382/131 |
| 2013/0054214 A1 | 2/2013 | Taylor |
| 2013/0064438 A1 | 3/2013 | Taylor et al. |
| 2013/0132054 A1* | 5/2013 | Sharma ............... G16B 5/00 703/9 |
| 2013/0246034 A1* | 9/2013 | Sharma ............... A61B 5/02007 703/11 |
| 2014/0058715 A1 | 2/2014 | Sharma et al. |
| 2014/0073976 A1* | 3/2014 | Fonte ............... A61B 6/504 600/504 |
| 2015/0112182 A1 | 4/2015 | Sharma et al. |
| 2015/0324962 A1* | 11/2015 | Itu ............... G06T 7/00 382/130 |
| 2015/0335304 A1* | 11/2015 | Lavi ............... G06F 19/321 600/407 |
| 2015/0374243 A1* | 12/2015 | Itu ............... G16H 50/50 703/2 |
| 2017/0004278 A1* | 1/2017 | Marsden ............... G06F 17/5018 |
| 2017/0018081 A1* | 1/2017 | Taylor ............... A61B 6/032 |

OTHER PUBLICATIONS

Chamuleau et al., "Association between coronary lesion severity and distal microvascular resistance in patients with coronary artery disease," Am J Physiol Heart Circ Physiol, vol. 285, pp. H2194-H2200, 2003.

De Bruyne et al., "Simultaneous Coronary Pressure and Flow Velocity Measurements in Humans," Circulation, vol. 94, pp. 1842-1849, 1996.

H. Vernon Anderson et al., "Coronary Atery Flow Velocity is Related to Lumen Area and Regional Left Ventricular Mass," Circulation, vol. 102, pp. 48-54, 2000.

\* cited by examiner

200

210

220

230

METHOD AND SYSTEM FOR ENHANCING MEDICAL IMAGE-BASED BLOOD FLOW COMPUTATIONS USING PHYSIOLOGICAL MEASUREMENTS

This application claims the benefit of U.S. Provisional Application No. 62/197,204, filed Jul. 27, 2015, the disclosure of which is herein incorporated by reference.

BACKGROUND OF THE INVENTION

The present invention relates to medical-image based blood flow computations for simulating blood flow in a patient's vessels, and more particularly, to enhancing medical image-based blood flow computations using invasive physiological measurements.

Cardiovascular disease (CVD) is the leading cause of deaths worldwide. Among various CVDs, coronary artery disease (CAD) accounts for nearly fifty percent of those deaths. Local narrowing of a blood vessels, or stenosis, represents an important cause of cardiovascular diseases. Such stenoses typically develop gradually over time, and can develop in different parts of the arterial circulation, such as the coronary arteries, renal arteries, peripheral arteries, carotid artery, cerebral artery, etc. Such a local narrowing can also be the result of a congenital defect. One therapy widely used for treating arterial stenosis is stenting, i.e., the placement of a metal or polymer stent in the artery to open up the lumen, and hence facilitate the flow of blood. When dealing with coronary artery stenosis, the stenting therapy is referred to as percutaneous coronary intervention (PCI).

In recent years, there has been considerable focus on computational approaches for modeling the flow of blood in the human cardiovascular system. Blood flow computations, performed using computational fluid dynamics (CFD) algorithms, when used in conjunction with patient-specific anatomical models extracted from medical images, have been proposed for diagnosis, risk stratification, and surgical planning. Model-based assessment of the coronary circulatory system has been performed using such techniques applied to anatomical models reconstructed from coronary computed tomography angiography (CCTA) or x-ray coronary angiography (CA) in order to computer fractional flow reserve (FFR).

The input data used in personalized models for computing blood flow is obtained from medical imaging data. The personalization procedure, whose main goal is to estimate values of the model parameters such that the model accurately represents the subject-specific state of the cardiovascular system, uses input information from the medical imaging data, non-invasive measurements, and other population average assumptions, and requires a series of assumptions on certain physiological parameters. For example, the personalization procedure assumes that the coronary bed has a predictable reaction to hyperemia and the hyperemic-to-rest resistance ratio is fairly stable across different individuals. This assumption may not be true in cases in which micro-vessel disease is present, and the reduction in resistance may also vary from one patient to the next due to differences in age, gender, previous myocardial infarction, distal diffuse disease, etc. Further, the personalization procedure also assumes a relationship between vessel diameter and flow, which may not hold for every individual. In light of such assumptions, there may be mismatches between true hemodynamic indices and the hemodynamic indices computed from blood flow computations based on physiological principles.

BRIEF SUMMARY OF THE INVENTION

The present invention provides a method and system for simulating blood flow in a vessel of a patient to estimate hemodynamic quantities of interest using enhanced blood flow computations based on invasive physiological measurements of the patient. Embodiments of the present invention provide a comprehensive methodology for combining computational modeling techniques for simulating blood flow and invasive physiological measurements.

In one embodiment of the present invention, non-invasive patient data including medical image data and non-invasive clinical measurements of a patient are received. A patient-specific anatomical model of at least one vessel of the patient is generated from the medical image data. An invasive physiological measurement of the patient is received. A computational blood flow model for simulating blood flow in the patient-specific anatomical model of the at least one vessel of the patient is personalized based at least in part on the invasive physiological measurement of the patient. Blood flow is simulated in the patient-specific anatomical model of the at least one vessel of the patient and one or more hemodynamic quantities of interest are computed using the personalized computational blood flow model.

In another embodiment of the present invention, non-invasive patient data including medical image data and non-invasive clinical measurements of a patient are received. A patient-specific anatomical model of at least one vessel of the patient is generated from the medical image data. Blood flow is simulated in the patient-specific anatomical model of the at least one vessel of the patient and at least one hemodynamic quantity of interest is computed using a personalized computational blood flow model generated based on the non-invasive patient data. At least one measured hemodynamic quantity of interest resulting from invasive physiological measurements of the patient is received. The at least one computed hemodynamic quantity of interest is compared with the at least one measured hemodynamic quantity of interest, and an indication of specific patient condition is generated in response to a difference between the at least one computed hemodynamic quantity of interest and the at least one measured hemodynamic quantity of interest being greater than a threshold value.

These and other advantages of the invention will be apparent to those of ordinary skill in the art by reference to the following detailed description and the accompanying drawings.

DETAILED DESCRIPTION

Figure 1:
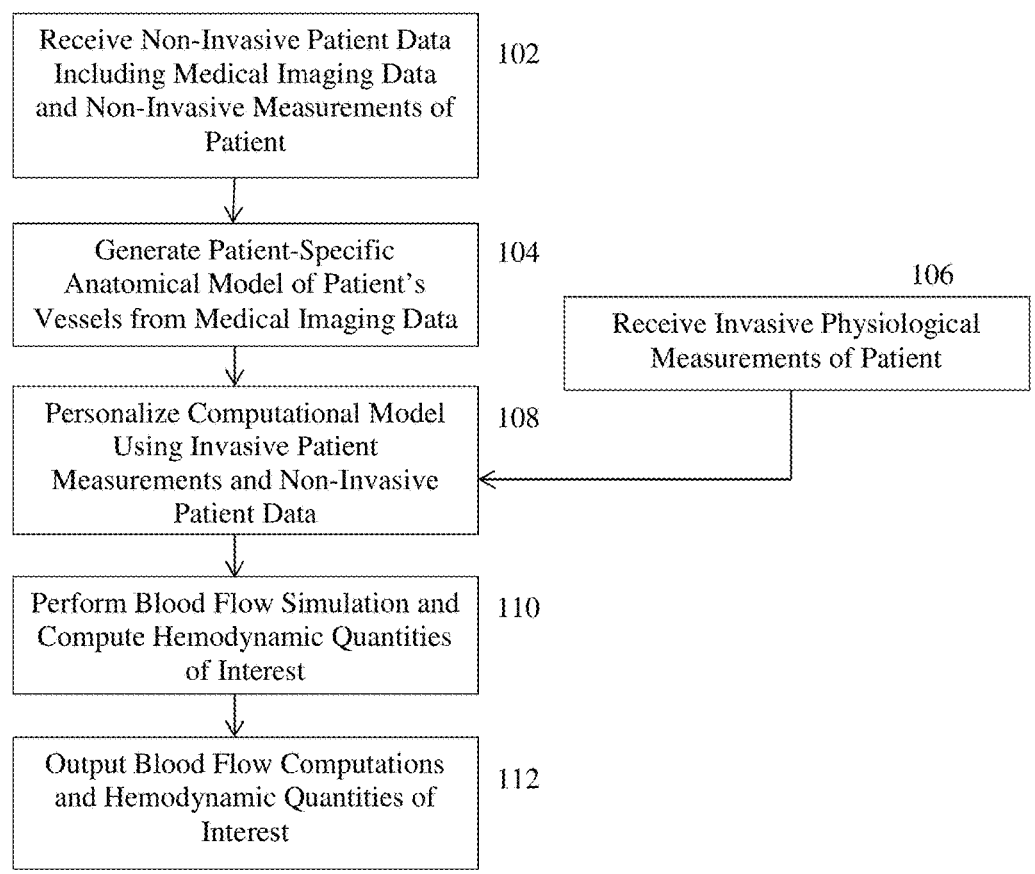
FIG. 1 illustrates a method for patient-specific blood flow simulation to estimate hemodynamic quantities of interest using enhanced blood flow computations based on invasive physiological measurements, according to an embodiment of the present invention.

The present invention relates to a method and system for simulating blood flow in a vessel of a patient to estimate hemodynamic quantities of interest using enhanced blood flow computations based on invasive physiological measurements of the patient. Embodiments of the present invention are described herein to give a visual understanding of the methods for simulating blood flow with enhanced blood flow computations. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a comprehensive methodology for combining computational modeling techniques for simulating blood flow and invasive physiological measurements. Computational modeling techniques are typically used to simulate blood flow in a patient's vessel to provide non-invasive computation of hemodynamic quantities of interest, such as fractional flow reserve (FFR). However, such computational modeling techniques rely on assumptions that may not hold for all patients, and therefore have not been widely accepted in clinical workflows for assessing severity of cardiovascular disease in patients. Embodiments of the present invention may be applied to utilize computational modeling (e.g., computational fluid dynamics (CFD) blood flow computations) in a clinical workflow in which one or more invasive physiological measurements is acquired for the patient. The use of the computational modeling combined with the invasive physiological measurements can decrease the amount of physical measurements necessary to determine hemodynamic quantities of interest, while improving the accuracy of the computational modeling techniques and compensating for situations in which assumptions relied on in computational modeling techniques do not apply for the patient. Although embodiments of the present invention described herein refer specifically to coronary circulation, the present invention is not limited thereto, and embodiments of the present invention may be similarly applied for other parts of the cardiovascular system, such as for renal arteries, cerebral arteries, the aorta, etc.

After introducing an overall method for patient-specific blood flow simulation to estimate hemodynamic quantities of interest using enhanced blood flow computations based on invasive physiological measurements, a set of novel use cases are described herein. In one embodiment, a methodology for estimating the index of microvascular resistance (IMR) is provided, in which a single invasive physiological measurement (e.g., pressure, velocity, or transit time) is used in combination with a computational model. Otherwise, a fully invasive evaluation of IMR would require two different invasive measurements (typically pressure and transit time measurements). Other embodiments provide workflows for enhancing the results of computational models when the state of the patient during the invasive measurement is either the same or different. Another embodiment provides a workflow for generating an indication of a specific patient condition to a clinician. Another embodiment provides a workflow in which invasive medical imaging techniques are combined with non-invasive medical imaging techniques to obtain a better anatomical reconstruction of the patient's vessels.

FIG. 1 illustrates a method for patient-specific blood flow simulation to estimate hemodynamic quantities of interest using enhanced blood flow computations based on invasive physiological measurements, according to an embodiment of the present invention. The method of FIG. 1 transforms medical image data representing vessels of a patient to generate a patient-specific anatomical model of the patient's vessels and simulate blood flow in the patient's vessels.

Referring to FIG. 1, at step 102 non-invasive patient data including medical imaging data and non-invasive measurements of the patient is received. Medical imaging data from one or multiple imaging modalities can be received. For example, the medical imaging data can include, computed tomography (CT), Dyna CT, magnetic resonance (MR), Angiography, Ultrasound, Single Photon Emission computed Tomography (SPECT), and any other type of non-invasive medical imaging modality. The medical image data can be 2D, 3D, or 4D (3D+time) medical image data. The medical image data can be received directly from one or more image acquisition devices, such as a CT scanner, MR scanner, Angiography scanner, Ultrasound device, etc., or the medical image data may be received by loading previously stored medical image data for a patient.

In an advantageous embodiment, 3D coronary CT angiography (CTA) images are acquired on a CT scanner. The CTA images ensure that coronary vasculature, including the vessel(s) that contain the stenosis, is adequately imaged using a contrast agent that is injected into the patient. At this stage, the clinician may be provided with an option of identifying lesions (stenoses) of interest by interactively viewing them on the images. This step can also be performed on a patient-specific anatomical model that is extracted from the image data (step 104). Alternatively, the stenoses may be automatically detected in the image data using an algorithm for automatic detection of coronary artery stenosis, such as the method for automatic detection of coronary artery stenosis described in United States Published Patent Application No. 2011/0224542, which is incorporated herein by reference. In addition to the medical image data, other non-invasive clinical measurements, such as the patient's heart rate and systolic and diastolic blood pressure may also be acquired.

At step 104, a patient-specific anatomical model of the patient's vessels is extracted from the medical imaging data. The patient-specific anatomical model may be a patient-specific anatomical model of vessels in any portion of the patient's cardiovascular system. In an exemplary embodiment, the patient-specific anatomical model is a patient-specific anatomical model of full coronary artery tree of the patient or a partial coronary artery tree of the patient. In order to generate a patient-specific anatomical model of the coronary artery tree, the coronary arteries can be segmented in the 3D medical image data using an automated coronary artery centerline extraction algorithm. For example, the coronary arteries can be segmented in a CT volume using the method described United States Published Patent Application No. 2010/0067760, which is incorporated herein by reference. Once a coronary artery centerline tree is extracted, cross-section contours can be generated at each point of the centerline tree. The cross-section contour at each centerline point gives a corresponding cross-section area measurement at that point in the coronary artery. A geometric surface model is then generated for the segmented coronary arteries. For example, methods for anatomical modeling of the coronary arteries are described in U.S. Pat. Nos. 7,860,290 and 7,953,266, both of which are incorporated herein by reference. In addition to the coronaries, the patient-specific anatomical model can include the aortic root together with the proximal part of the aorta. A detailed 3D model of each stenosis in the patient's vessels (e.g., coronary arteries) can also be extracted using similar algorithms, which includes the quantification of the proximal vessel diameter and area, distal vessel diameter and area, minimal lumen diameter and area, and length of stenosis.

Figure 2:
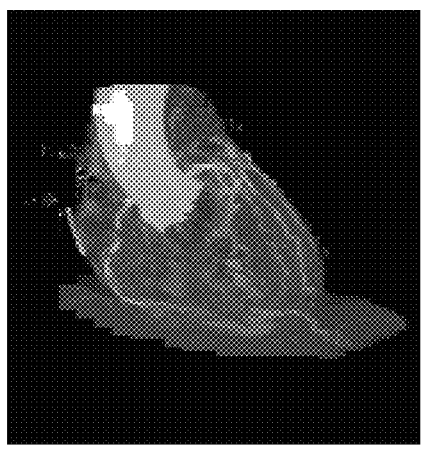
FIG. 2 illustrates exemplary results for generating a patient-specific anatomical model of the coronary vessel tree.
Figure 2:
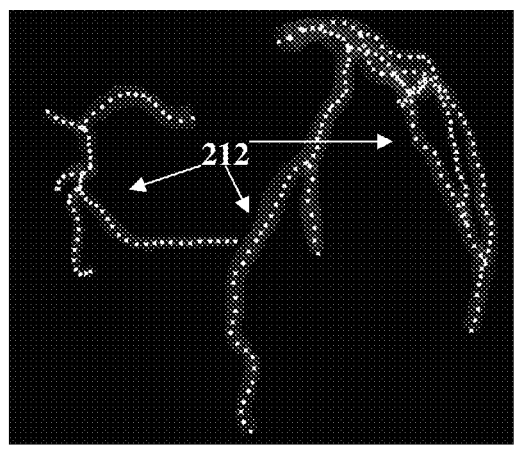
Figure 2:
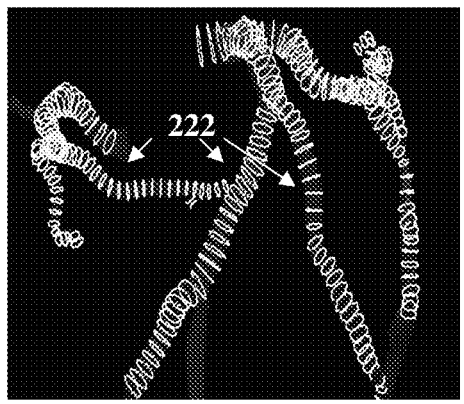
Figure 2:
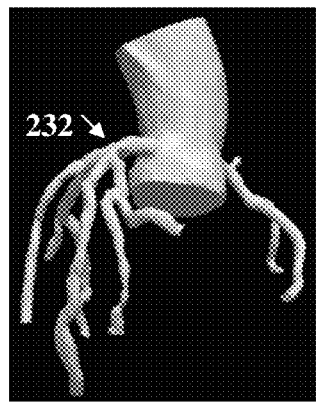

FIG. 2 illustrates exemplary results for generating a patient-specific anatomical model of the coronary vessel tree. Image 200 of FIG. 2 shows coronary CTA data. Image 210 shows a centerline tree 212 extracted from the CTA data. Image 220 shows cross-section contours 222 extracted at each point of the centerline tree 212. Image 230 shows a 2D surface mesh 232 of the coronary arteries, the aortic root, and the proximal part of the aorta. It is to be understood that the anatomical model of the coronary tree of the patient can be output and displayed, for example on a display screen of the computer system.

The above described anatomical modeling tasks can be performed automatically or can be user-driven, thereby allowing the user (clinician) to interactively make changes to the anatomical models to analyze the effects of such changes on the subsequent computation of FFR. In addition to the coronary vessel tree, the myocardium may also be segmented (either automatically or manually) in the medical image data to determine an estimate of the left ventricular mass, which in a possible implementation, may be used to estimate the absolute resting flow for the patient which can be used to calculate boundary conditions for a computational blood flow and pressure simulation. Alternatively, the resting flow could also be computed based on the total volume of the segmented coronary tree, or from the outlet radius of the different coronary vessels. In an exemplary embodiment, a patient-specific anatomical model of the heart that is automatically generated from the image data may be used for this purpose. The anatomical heart model is a multi-component model having multiple cardiac components, including the four chambers (left ventricle, left atrium, right ventricle, and right atrium). The anatomical heart model may also include components such as the heart valves (aortic valve, mitral valve, tricuspid valve, and pulmonary valve) and the aorta. Such a comprehensive model of the heart is used to capture a large variety of morphological, functional, and pathological variations. A modular and hierarchical approach can be used to reduce anatomical complexity and facilitate an effective and flexible estimation of individual anatomies. The 4D anatomical heart model can be generated by generating individual models of each heart component, for example using marginal space learning (MSL), and then integrating the heart component models by establishing mesh point correspondence. Additional details regarding generation of such a 4D patient-specific heart model are described in United States Published Patent Application No. 2012/0022843, which is incorporated herein by reference in its entirety.

Returning to FIG. 1, at step 106, invasive physiological measurements of the patient are received. For example such invasive physiological measurements may include invasive measurements of one or more of pressure, flow rate, velocity, etc. in a patient's vessel acquired using sensors on guidewires or catheters inserted into the vessel. The invasive physiological measurements may also include invasive medical imaging data, such as angiography or intravascular ultrasound (IVUS), in which internal images of the patient's vessel are acquired using a probe inserted into the patient's vessel.

At step 108, a computational blood flow model is personalized based on the invasive physiological measurements and the non-invasive patient data. The computational blood flow model is constructed based on the patient-specific anatomical model of the patient's vessels and used to simulate blood flow and pressure in the patient-specific anatomical model using CFD computations or any other standard numerical technique, such as finite-element method, finite-difference method, finite volume method, boundary element method, embedded boundary method, immersed boundary method lattice Boltzmann method, etc., to computed blood flow and pressure values at locations in the patient-specific anatomical model over a plurality of time steps. In a possible implementation, one or more of the parameters or boundary conditions of the computational blood flow model can be personalized based on the non-invasive patient data, such as the medical image data, the patient-specific anatomical model extracted from the medical image data, and/or the non-invasive patient measurements, and one or more parameters or boundary conditions of the computational blood flow model can be personalized based on the invasive physiological measurements or a combination of the non-invasive patient data and the invasive physiological measurements. In a possible implementation, the parameters and boundary conditions of the computational blood flow model can be initially personalized using the non-invasive patient data, and then one or more of the parameters or boundary conditions can be adjusted or "re-personalized" based on the invasive physiological measurements. In another possible implementation, the model can be personalized based on the invasive physiological measurements by reconstructing the patient-specific anatomical model based on the invasive physiological measurements (e.g., based on invasive medical imaging data) to generate an improved patient-specific anatomical model, and then personalizing the computational blood flow model based on the improved patient-specific anatomical model.

Figure 3:
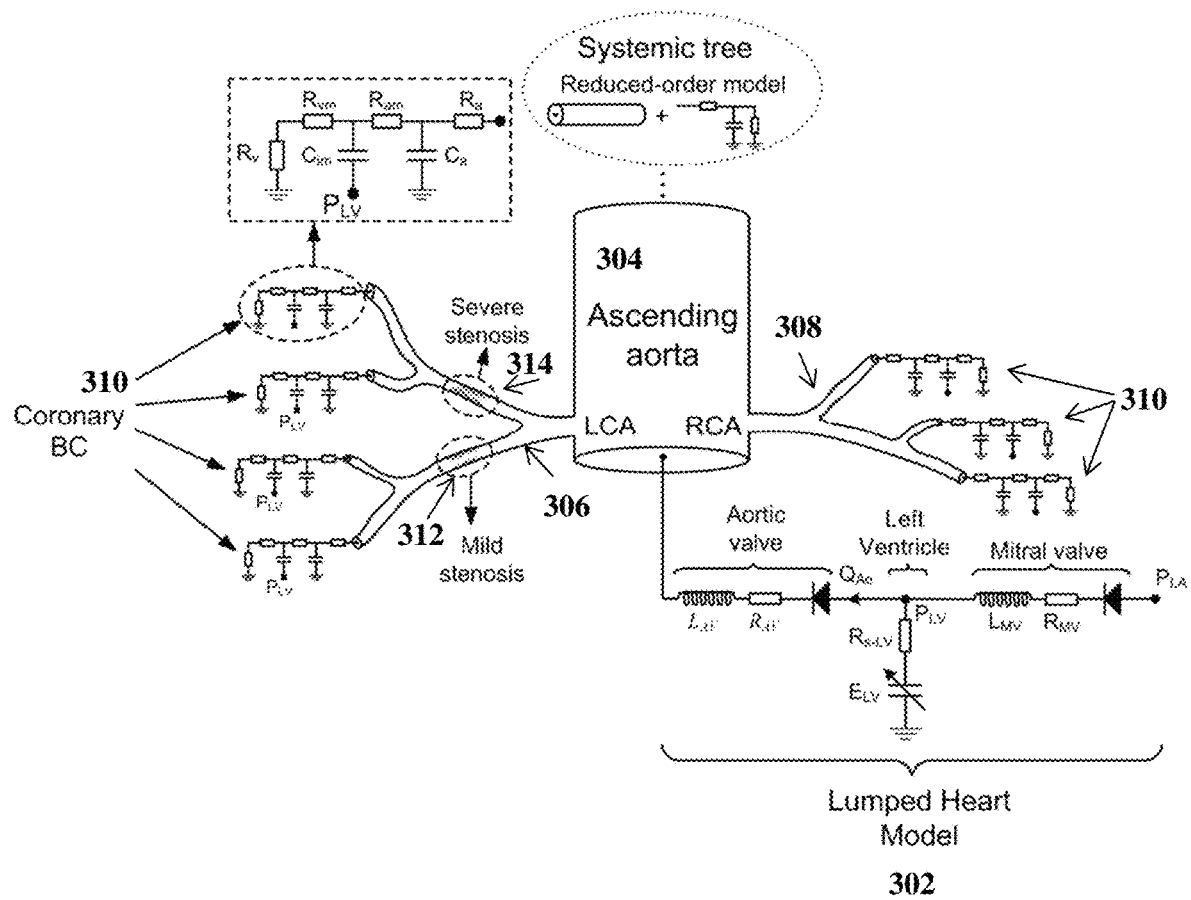
FIG. 3 illustrates an exemplary multi-scale computational model of coronary circulation according to an embodiment of the present invention.

According to an exemplary embodiment of the present invention, a multi-scale computational model of coronary circulation can be used to compute the blood flow and pressure in a patient-specific anatomical model of the coronary arteries over a series of time steps. For example, the simulation may be performed for a plurality of time steps corresponding to a full cardiac cycle or multiple cardiac cycles. The computational model of the coronary circulation models the loss of pressure across stenoses or other narrowings in the coronary arteries (e.g., calcification, thrombus, bifurcation, etc.) using pressure-drop models. FIG. 3 illustrates an exemplary multi-scale computational model of coronary circulation according to an embodiment of the present invention. As shown in FIG. 3, a heart model 302 is coupled at the root of the aorta. The heart model 302 may be implemented as a lumped model parameterized through patient-specific data as shown in FIG. 3, or may be implemented as a full 3D heart model. Large arteries, such as the aorta 304 together with the large arteries supplied by the aorta (e.g., subclavian, brachiocephalic, common carotid, etc.), the left coronary artery (LCA) 306, and the right coronary artery (RCA) 308 can be represented as 1D blood flow models or full 3D models. Furthermore, semi-analytical circulatory models can be used either separately for certain arterial segments, or embedded within the 1D or 3D models. The vessel walls can be modeled as a purely elastic or visco-elastic material. The wall properties may be determined through an empirical relationship fit to measured data or based on patient-specific estimations of wall compliance. In the model of coronary arterial circulation of FIG. 3, all microvascular beds are simulated through lumped parameter models 310 which account for the resistance applied to the blood flow and for the compliance of the distal vessels. The coronary vascular bed is modeled through such lumped parameter models 310, which are adapted to the coronary circulation in the sense that they take into account the effects of the myocardial contraction on the flow waveform.

Stenosis segments 312 and 314 (i.e., regions in the vessels where a stenosis or a narrowing is detected) are shown in the model of coronary arterial circulation. It is to be understood that the term stenosis is used herein to generally refer to any type of narrowing in a vessel. The stenosis segments 312 and 314 cannot be simulated using the 1D blood flow models since there is a high variation in cross-sectional area and the shape of the stenosis influences the blood flow behavior and especially the trans-stenotic pressure drop which plays a major role in the assessment of the functional importance of such a stenosis. According to an advantageous implementation, a reduced-order (as compared to a full 3D model) pressure-drop model can be used for each stenosis segment 312 and 314. The pressure drop model for a particular stenosis computes the pressure drop over the stenosis due to the narrowing of the vessel without performing an explicit flow computation in that region of the vessel. Various pressure-drop models can be used. For example, the pressure-drop model for a stenosis may be a fully analytical model or may be a model that includes a combination of analytical and empirical terms, referred to herein as a "semi-empirical pressure-drop model". Other pressure-drop models may be used as well, such as a machine-learning based pressure-drop model that is trained using a machine-learning algorithm to map anatomical and flow features derived from a stenosis to a pressure-drop associated with the stenosis. Additional details regarding the multi-scale computational model of coronary circulation, as well as calculating rest-state and hyperemia-state boundary conditions for the blood flow and pressure computations, are described in United States Patent Publication No. 2013/0132054, entitled "Method and System for Multi-Scale Anatomical and Functional Modeling of Coronary Circulation," United States Patent Publication No. 2013/0246034, entitled "Method and System for Non-Invasive Functional Assessment of Coronary Artery Stenosis," and United States Patent Publication No. 2014/00058715, entitled "Method and System for Non-Invasive Functional Assessment of Coronary Artery Stenosis," and U.S. application Ser. No. 14/689,083, entitled "Method and System for Non-Invasive Computation of Hemodynamic Indices for Coronary Artery Stenosis," which are incorporated herein in their entirety by reference.

Returning to FIG. 1, at step 110, blood flow simulations are performed using the personalized computational model and hemodynamic quantities of interest are computed based on the blood flow simulations. In particular, the personalized computational model computed blood flow and pressure values at each of a plurality of points in the patient-specific anatomical model of the patient's vessels over a plurality of time steps. Hemodynamic quantities of interest, such as fractional flow reserve (FFR), coronary flow reserve (CFR), index of microvascular resistance (IMR), instantaneous wave-free ratio (iFR), basal Pd/Pa, basal stenosis resistance, hyperemic stenosis resistance, indication of previous myocardial infarction, etc., can be calculated from the computed blood flow and/or pressure values. At step 112, the blood flow and pressure computations and the hemodynamic quantities of interest are output. For example, the computed hemodynamic quantities of interest and/or the blood flow and pressure values computed for the plurality of points in the patient-specific anatomical model over the plurality of time steps can be output by displaying the hemodynamic quantities of interest and/or the blood flow and pressure computations on a display of a computer system.

The method of FIG. 1 can be applied to various use cases according to various embodiments of the present invention. In some embodiments, the patient state (e.g., rest, exercise, hyperemia, pre-intervention, post-intervention, etc.) during the acquisition of the invasive physiological measurement at step 106 may be different from the patient state that is simulated during the blood flow computation performed at step 110. In some embodiments, the invasively measured quantity acquired at step 106 may be different from the hemodynamic quantity of interest computed at step 110. For example, in the case of coronary hemodynamic computations, the computed hemodynamic quantities of interest may include one or more of fractional flow reserve (FFR), coronary flow reserve (CFR), index of microvascular resistance (IMR), instantaneous wave-free ratio (iFR), basal Pd/Pa, basal stenosis resistance, hyperemic stenosis resistance, indication of previous myocardial infarction, etc. In some embodiments, the blood flow computation performed at step 110 may be performed for different vessel regions/trees than the ones where the invasive measurement acquired at step 106 was performed.

Estimating the Index of Microvascular Resistance

In one embodiment, the method of FIG. 1 can be applied to estimate the index of microvascular resistance (IMR) for a patient. The role of microvasculature in the functional assessment of coronary stenosis has often been underestimated. Typically, the functional assessment is performed at hyperemia, when the flow is maximal due to a maximally dilated microvasculature. However, if microvascular disease is present, the flow is limited to a lower value. Hence, the pressure drop across the stenoses becomes smaller and a negative FFR value may be measured, indicating that there is no myocardial infarction risk for the patient. In reality, since in this case the flow is limited mainly by the microvasculature, and not by the epicardial stenosis interrogated through FFR, the patient may in fact be at high risk of suffering a heart attack. The higher the impairment of the microvascular function, the more severe is the underestimation of the stenosis severity. Microvascular disease may be caused by coronary micro-embolisation, peri-interventional reflex coronary vasomotion, or structural remodeling.

The presence of microvascular disease, alongside coronary diffuse disease, is the main cause for the discordance that has been clinically observed between CFR and FFR. Significant microvascular disease limits the maximal flow, which leads to a low CFR value (indicative of a positive diagnosis—meaning that a patient is at risk of a heart attack), and to a high FFR value (indicative of a negative diagnosis). Clinically, to evaluate the function of both epicardial stenoses and the microvasculature, two different measurements are required. These may be any two measurements from the following: pressure, flow (velocity), or transit time measurements. Pressure and flow (velocity) measurements may be used to determine FFR and CFR. Pressure measurements and transit time estimations may be used to determine FFR and IMR.

The index of microvascular resistance (IMR) is a coronary diagnostic index which is a measure invasively and evaluates the coronary microvascular function. Typically, a combined pressure and temperature tipped guidewire is used for the measurement of IMR. The coronary microvascular resistance can be defined as:

$$R = \frac{P_d - P_v}{Q}, \quad (1)$$

where $P_d$ is the distal epicardial pressure, $P_v$ is the venous pressure, and Q is the flow rate. The flow rate in turn may be computed from measurements performed for a region of interest:

$$Q = \frac{V}{T} \approx \frac{1}{T}, \quad (2)$$

where V is the vessel volume in the region of interest and T is the time required for the blood to pass that region of interest. Hence, Q is inversely proportional to the transit time T. By additionally neglecting the venous pressure in Equation (1), the index of microvascular resistance (IMR) is defined as:

$$IMR = P_d \cdot T. \quad (3)$$

In practice, IMR is typically defined for the hyperemic state as distal coronary pressure time the mean transit time of a 3 ml saline bolus. IMR is used to assess the microvascular function of patients suspected to have coronary artery disease. Previous studies have shown that the IMR is higher in patients with microvascular obstruction (MVO) than in patients without MVO. Furthermore, IMR was also has also been shown to be a reliable index for predicting left ventricular function recovery in patients with acute myocardial infarction.

A completely non-invasive tool, such as previous computational blood flow models, is not able to simultaneously evaluate the function of coronary epicardial stenoses and the coronary microvasculature. According to an embodiment of the present invention, a computational blood flow model is combined with invasive measurements to derive a comprehensive evaluation of the coronary physiology of the heart.

Figure 4:
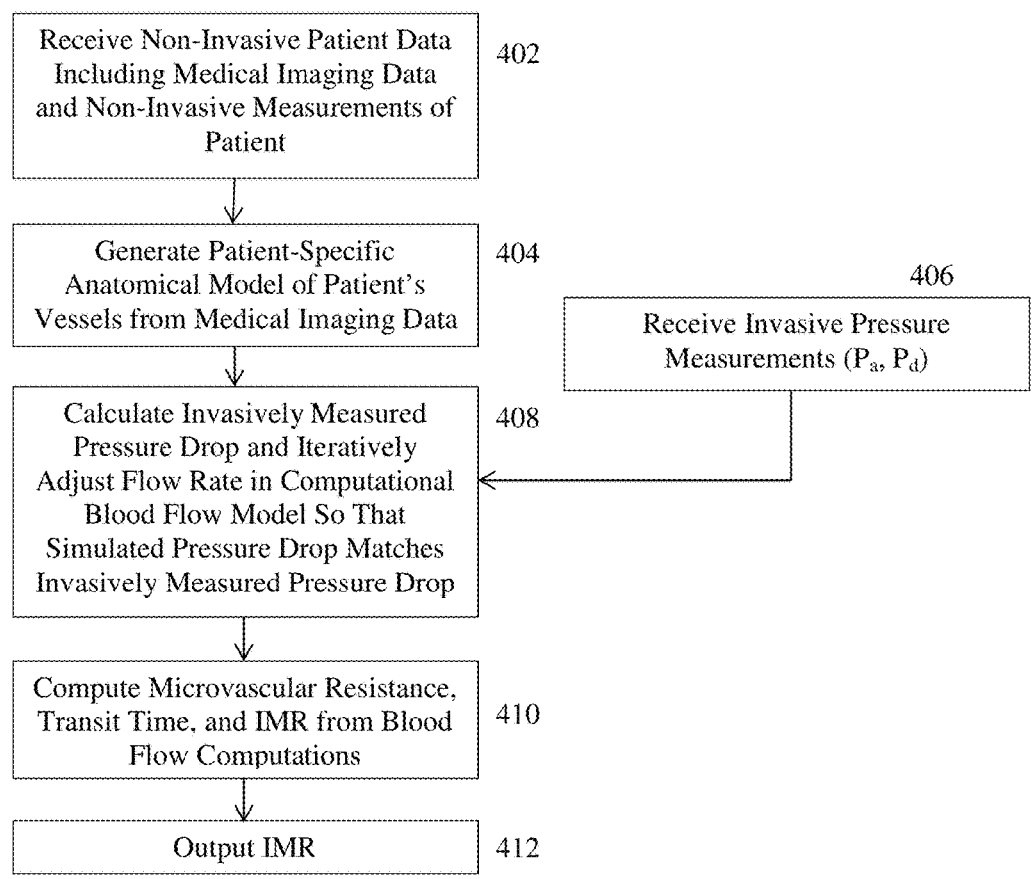
FIG. 4 illustrates a method for estimating the index of microvascular resistance (IMR) by combining an invasive physiological measurement with a computational blood flow model according to an embodiment of the present invention.

FIG. 4 illustrates a method for estimating the index of microvascular resistance (IMR) by combining an invasive physiological measurement with a computational blood flow model according to an embodiment of the present invention. Steps 402 and 404 of the method of FIG. 4 are the same as steps 102 and 104 of FIG. 1, and can be implemented as described above in connection with FIG. 1. At step 406, invasive pressure measurements are received. For example, the invasive pressure measurements can be acquired using a pressure wire that is inserted into the patient's vessel. The invasive pressure measurements may be used to determine cycle-averaged aortic pressure ($P_a$) and cycle-averaged distal pressure ($P_d$) distal to a stenosis. At step 408, in order to personalize the computational blood flow model based on the invasive pressure measurements, an invasively measured pressure drop is calculated and the flow rate in the computational model is iteratively adjusted so that the simulated pressure drop resulting from the computational model matches the invasively measured pressure drop. In particular, a stenosis specific invasively measured pressure drop for a particular stenosis is calculated as $\Delta P = P_a - P_d$. The computational blood flow model is then run iteratively to determine a flow rate Q through the stenosis which results in a simulated pressure drop for the stenosis computed using the computational blood flow model that matches the invasively measured pressure drop for the stenosis. At step 410, the microvascular resistance, transit time, and IMR are computed from the blood flow computations using the personalized computational blood flow model. In particular, once the flow rate Q through the stenosis is determined, the microvascular resistance may be calculated as:

$$R = \frac{P_d}{Q}. \quad (4)$$

The transit time T can be computed based on the flow rate Q using Equation (2), and the IMR can be computed from $P_d$ and the transit time T using Equation (3). Accordingly, in the method of FIG. 4 only a single invasive physiological measurement (pressure) is needed to estimate IMR. At step 412, the computed IMR value is output, for example, by displaying the computed IMR value on a display device of a computer system. Other computed values, such as the computed microvascular resistance, transit time, and/or blood flow may be output as well.

In another embodiment for estimating IMR, the coronary flow velocity v may be measured invasively (instead of the pressure), for example using a guide wire inserted into the patient's vessel or ultrasound dilution blood flow measurements. In order to personalize the computational model based on the invasive velocity measurement, the flow rate Q through the vessel (e.g., through a stenosis in the vessel) may then be computed using the velocity v and the cross-sectional area A of the vessel in the patient-specific anatomical model:

$$Q = v \cdot A. \quad (5)$$

This flow rate is imposed in the computational blood flow model and the pressure drop $\Delta P$ over the stenosis is simulated (computed) by the computational blood flow model. The average aortic pressure $P_a$ may be estimated for non-invasively acquired cuff-based pressure measurements, and the distal pressure $P_d$ may be determined as:

$$P_d = P_a - \Delta P. \quad (6)$$

The microvascular resistance, transit time, and IMR can then be calculated using Equations (4), (2), and (3), respectively. In this embodiment, only a single invasive physiological measurement (flow velocity) is needed to estimate IMR.

In yet another embodiment for estimating IMR, the transit time T may be measured invasively. For example, the transit time T may be invasively measured by measuring the mean transit time of a 3 ml saline bolus. Alternatively, the transit time may be extracted from Angio images recorded at hyperemia, by analyzing the transport of the contrast agent. In order to personalize the computational model based on the invasive velocity measurement, the flow rate Q through the vessel (e.g., through a stenosis in the vessel) may then be computed based on the transit time and the volume of the vessel in the patient-specific anatomical model using Equation (2). This flow rate is imposed in the computational blood flow model and the pressure drop $\Delta P$ over the stenosis is simulated (computed) by the computational blood flow model. The average aortic pressure $P_a$ may be estimated for non-invasively acquired cuff-based pressure measurements, and the distal pressure $P_d$ may be determined using Equation (6). The microvascular resistance and IMR can then be computed using Equations (4) and (3), respectively. In this embodiment, only a single invasive physiological measurement (transit time) is needed to estimate IMR.

It can be noted that in all of the above describe embodiments for estimating IMR, a diagnostic index of the epicardial stenosis is also derived, either directly through measurement, or from the computational model. This index may be either the FFR or hyperemic stenosis resistance, which is an index that evaluates solely the functional significance of epicardial stenoses.

Functional Assessment of Coronary Artery Diffuse Disease

In another embodiment of the present invention, the method of FIG. 1 can be applied for functional assessment of coronary artery diffuse disease. As described above, coronary artery diffuse disease is a possible cause for discordance between CFR and FFR. Diffuse coronary artery disease (CAD) is often diagnosed in diabetic patients and may be present in the distal part of the vasculature or both the proximal and the distal part of the vasculature. When diffuse CAD is present only in the distal part of the vasculature, FFR appears normal, while CFR is reduced. When diffuse CAD is present in both the proximal and the distal part of the vasculature, both FFR and CFR are reduced. In this case, a discordance between FFR and angiographic observations is often discovered, since FFR may be low even though there is no angiographically significant stenosis.

Since previous computational tools are mainly based on geometric information from medical images, they are not able to correctly compute the coronary function of patients with diffuse disease. According to an advantageous embodiment of the present invention, as additional invasive pressure or velocity measurement may be used to obtain a correct functional assessment of the coronary arteries.

In one embodiment, invasive pressure measurements (e.g., acquired using a pressure wire inserted into the patient's vessel) may be received and used to determine cycle averaged aortic pressure ($P_a$) and cycle averaged distal pressure ($P_d$) for a stenosis. An invasively measured stenosis specific pressure drop is then calculated as $\Delta P = P_a - P_d$. In order to personalize the computational model, the computational model may be run iteratively in order to determine the flow rate Q through the stenosis which leads to a simulated trans-stenotic pressure drop computed using the computational model that matches the invasively measured pressure drop. Once the computational model is personalized by determining the flow rate Q, the personalized computational model performs blood flow simulations and computes the FFR and CFR from the blood flow simulations.

In another embodiment, the coronary flow velocity v may be measured invasively, for example using a guide wire inserted into the patient's vessel. Alternatively, the velocity may be determined from Angio images recorded at hyperemia, by analyzing the transport of the contrast agent. The computational blood flow model may be personalized by determining the flow rate Q using Equation (5) based on the velocity v and the cross-sectional area A of the vessel in the patient-specific anatomical model. This flow rate is imposed in the computational model and the pressure drop ($\Delta P$) for a stenosis is computed from the blood flow simulations performed by the computational blood flow model. The average aortic pressure $P_a$ may be estimated for non-invasively acquired cuff-based pressure measurements, and the distal pressure $P_d$ may be determined using Equation (6). FFR and CFR are computed from the blood flow simulations performed by the personalized computational blood flow model.

In another embodiment, perfusion imaging may be used to determine the maximal (hyperemic) flow of the patient, respectively CFR. Once this flow is determined, the pressures may be extracted from the computational model as described above. Any perfusion imaging technique may be used for this approach, such as SPECT, PET, Cardiac MR, or CT perfusion.

All of the above embodiments for functional assessment of coronary artery diffuse disease enable the determination of both FFR and CFR using only one invasive patient measurement and a computational model of coronary physiology. This enables a comprehensive assessment of the coronary function of the patient, even in cases in which the patient suffers from coronary artery diffuse disease.

Enhancement of Blood Flow Computations for the Same Patient State

Figure 5:
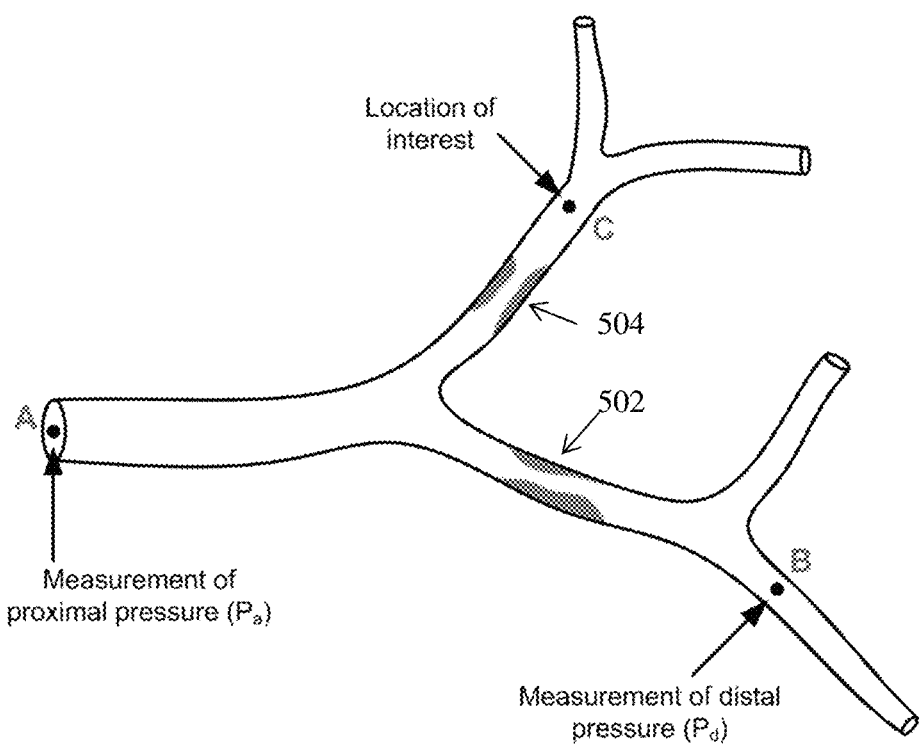
FIG. 5 illustrates an exemplary coronary artery geometry with two stenoses.

In another embodiment of the present invention, the method of FIG. 1 is applied to enhance blood flow computations for the same patient state. This embodiment refers to the specific configuration where the blood flow computation (step 110 of FIG. 1) and the invasive physiological measurements (step 106 of FIG. 1) are performed for the same patient state. We refer to coronary circulation herein, but similar approaches may be used for other parts of the cardiovascular system as well. FIG. 5 illustrates an exemplary coronary artery geometry with two stenoses 502 and 504. To diagnose a stenosis, typically the proximal or aortic pressure ($P_a$) and the distal pressure ($P_d$) are measured, and FFR is determined as the ratio between the cycle averaged $P_d$ and the cycle averaged $P_a$. For traditional calculation of FFR for the geometry of FIG. 5, $P_a$ is measured at location A, $P_d$ is measured at the distal locations B (distal to stenosis 502) and C (distal to stenosis 504) and distinct FFR values are computed for each distal location B and C.

A computational model may be used to estimate the value of FFR without performing invasive measurements (computed FFR is determined similarly to invasive FFR: the ratio between the computed average $P_d$ and the computed average $P_a$). In advantageous embodiment of the present invention, blood pressure values are invasively measured for the aortic pressure $P_a$ and the distal pressure $P_d$ distal to one of the stenoses, and these blood pressure values are used to perform a better personalization of the computational blood flow model. For example, the blood pressure values can be measured only at locations A and B in FIG. 5.

Figure 6:
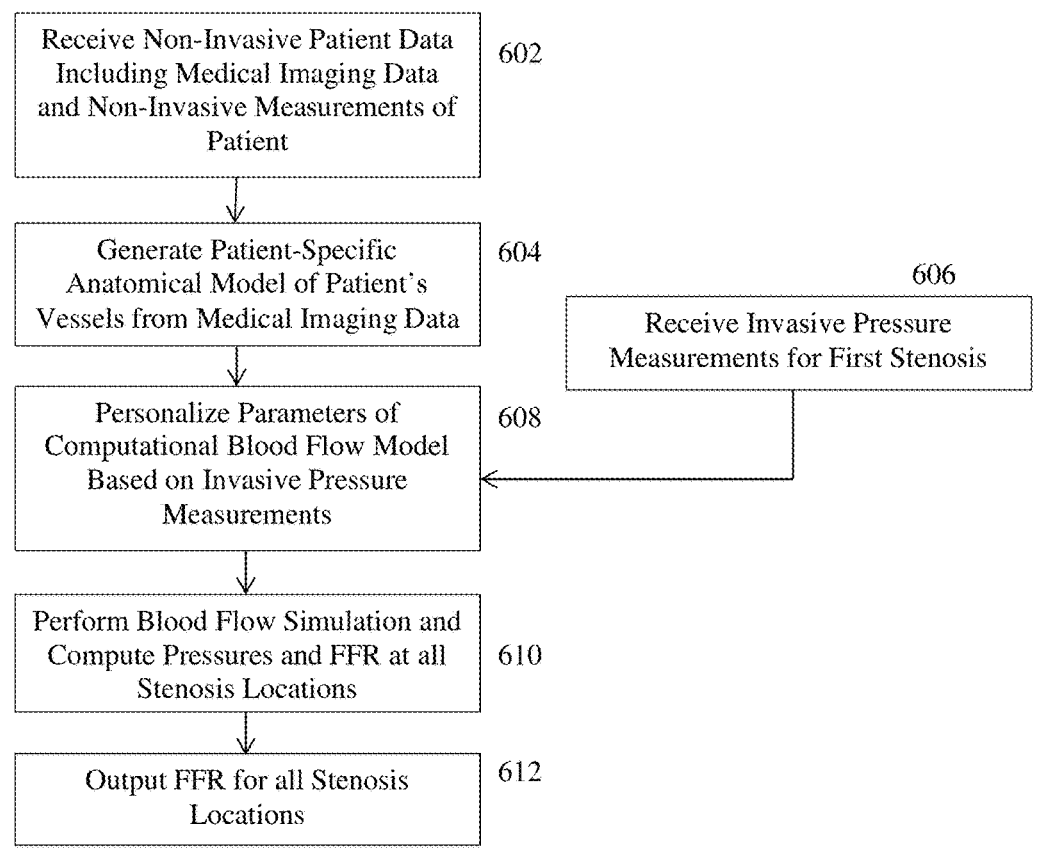
FIG. 6 illustrates a method enhancing blood flow computations based on invasive physiology measurements acquired at a patient state that is the same as the patient state for which the blood flow computations are performed.

FIG. 6 illustrates a method enhancing blood flow computations based on invasive physiology measurements acquired at a patient state that is the same as the patient state for which the blood flow computations are performed. Steps 602 and 604 of the method of FIG. 6 are the same as steps 102 and 104 of FIG. 1, and can be implemented as described above in connection with FIG. 1. At step 606, invasive pressure measurements are received for a first stenosis. For example, the invasive pressure measurements can be acquired using a pressure wire that is inserted into the patient's vessel. The invasive pressure measurements are acquired at a first location to measure a proximal or aortic pressure (e.g., location A in FIG. 5) and a second location (e.g., location B in FIG. 5) distal to a first stenosis (e.g., stenosis 502 in FIG. 5) to measure a distal pressure, and may be used to determine cycle-averaged aortic pressure and cycle-averaged distal pressure. At step 608, the computational blood flow model is personalized based on the invasive pressure measurements. The computational blood flow model may be personalized based on the invasive pressure measurements using one or more of the following approaches:

The measured aortic pressure may be used to compute the coronary microvascular resistances (which are determined as ratio between the average pressure and the flow rate at each outlet). Moreover, the aortic pressure can be used to directly specify the inlet boundary condition, or several characteristics of the measured aortic curve (systolic pressure, diastolic pressure, pulse pressure, average pressure, heart rate, presence/absence of dicrotic notch, time of aortic valve opening, time of aortic valve closure, etc.) may be extracted and then used to personalize the computations;

The flow rate may be adapted so as to match the instantaneous or the average pressure drop between the proximal and the distal location (for example, $Q=k \cdot r^n$, where Q is the flow rate, r is the radius, n is a power coefficient and k is a proportionality constant: the value of k may be adapted so as to obtain a match between computed and measured pressure drop);

The pressure-based inlet boundary condition may be adapted so as to match the instantaneous or the average pressure drop between the proximal and the distal location;

The parameters of the stenosis models may be adapted so as to match the instantaneous or the average pressure drop between the proximal and the distal location;

The outlet boundary conditions (i.e. the microvascular resistance) may be adapted so as to match the instantaneous or the average pressure drop between the proximal and the distal location;

If a heart model is used, its parameters may be adapted by using characteristics of the pressure curves: onset of systole is identified from the onset of pressure increase in the distal pressure, elastance characteristics and timings may be extracted from the systolic period of the aortic pressure Alternatively, velocity measurements may be performed at locations A and B and used in a similar fashion to improve the personalization of the parameters in the computational blood flow model. At step 610, the blood flow simulation is performed and FFR values are computed for all stenosis locations using the personalized computational blood flow model. Based on the computed pressure values in the blood flow simulation, FFR can be calculated at any point in the patient-specific anatomical model of the patient's vessel. Referring to FIG. 5, the FFR values are calculated at locations B and C distal to the stenoses 502 and 504, respectively. Since the modified parameter values affect the computed blood flow quantities in the entire coronary geometry and lead to a better match between measured and computed quantities, the computed pressure and the corresponding computed FFR value at location C will also better match the measured values. At step 612, the computed FFR values for also the stenoses are output, for example, by displaying the computed FFR values on a display of a computer system.

Figure 7:
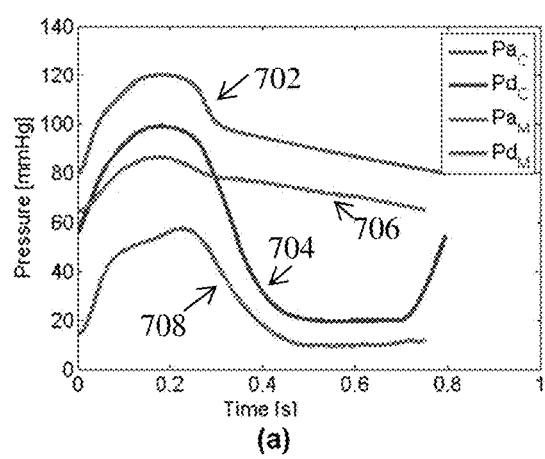
FIG. 7 illustrates a comparison of measured and computed pressures at locations A and C in the coronary geometry of FIG. 5 when invasive measurements are not used to personalize the computational blood flow model and when invasive measurements are used to personalize the computational blood flow model.
Figure 7:
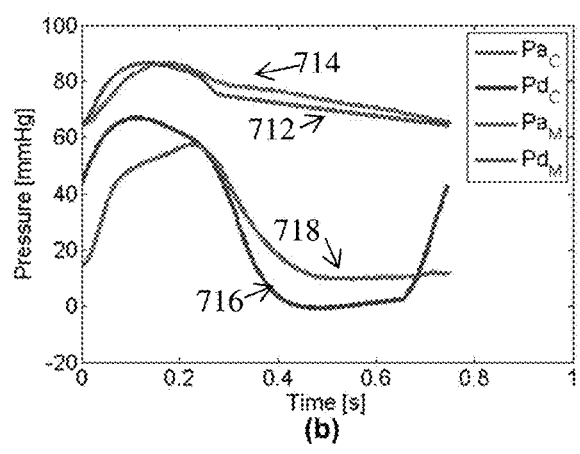

FIG. 7 illustrates a comparison of measured and computed pressures at locations A and C in the coronary geometry of FIG. 5 when invasive measurements are not used to personalize the computational blood flow model and when invasive measurements are used to personalize the computational blood flow model. Image (a) of FIG. 7 shows the computed aortic pressure 702 at location A and computed distal pressure 704 at location C computed without personalizing the computational blood flow model based on invasive pressure measurements, compared with the measured aortic pressure 706 at location A and the measured distal pressure 708 at location C. Image (b) of FIG. 7 shows the computed aortic pressure 712 at location A and computed distal pressure 714 at location C computed with the computational blood flow model personalized based on invasive pressure measurements acquired at locations A and B, compared with the measured aortic pressure 716 at location A and the measured distal pressure 718 at location C. The invasively measured FFR value at location C is 0.37. As shown in image (a), the aortic (702) and distal (704) coronary pressures computed without personalizing the computational blood flow model based on invasive pressure measurements substantially overestimate the invasively measured pressures (the computed FFR value at location C is 0.44). As shown in image (b), when the invasively measured aortic pressure and distal pressure at locations A and B are used to improve the estimation of personalized parameters of the computational model, the aortic (712) and the distal (714) coronary pressures computed using the hemodynamic simulation are superior (the computed FFR value at location C is 0.38).

Furthermore, compared to the current clinical practice, where invasive measurements are performed at all distal locations, the above described approach reduces the number of invasive measurements, which leads to several advantages, including:

The risk of complications (e.g. coronary artery dissection) is reduced;

The need for administering intracoronary vasodilating drugs is reduced; and

Due to technical issues, sometimes it is required to use more than one catheter equipped with pressure/velocity wire to perform all invasive measurements. Since fewer measurements are required this risk is diminished and costs may be reduced.

According to various embodiments of the present invention, there are other examples of invasively measured quantities which may be used to improve the results of the computational model. In an exemplary implementation, the venous pressure may be invasively measured and used for correct parameter estimation in the coronary microvascular models. The mean right atrial pressure may be used as surrogate measure for the venous pressure and may have a significant impact on invasively measured FFR. In another exemplary implementation, the end-diastolic ventricular pressure may be invasively measured and used for correct estimation of intramyocardial pressure. The intramyocardial pressure is the cause for the atypical flow rate profile in coronary arteries, with low systolic flow and high diastolic flow. It is generated by the ventricular contraction and is used in the coronary microvascular model. Left ventricular end diastolic pressure is positively associated with FFR.

The above described embodiments for enhancement of blood flow computations for the same patient state as the patient state at which the invasive physiological measurements are acquired may be used at any patient state (e.g., rest, hyperemia, exercise, pre-stenting, post-stenting). Furthermore, these embodiments may be used to enhance the computation of other hemodynamic indices in addition to FFR, such as Hyperemic Stenosis Resistance (HSR) and Basal Stenosis Resistance (BSR). HSR can be computed as $HSR=\Delta P/v_{hyper}$, where $\Delta P$ is the pressure drop between the aorta and distal location, and $v_{hyp}$ is the blood flow velocity, both under hyperemic conditions. The measured aortic and distal pressures may be used to enhance the results of the blood flow computation, e.g., so as to match the minimum/maximum/average measured pressure values. By matching the pressure values, the computed blood flow rate and velocity improve and lead to a superior estimation of the HSR index. Alternatively, only the coronary flow velocity may be measured and used to enhance the results of the blood flow computation. This would lead to an improvement in the computed pressure drop between coronary ostium and distal location and lead to a superior estimation of the HSR index. BSR can be computed as $BSR=\Delta P/v_{rest}$, where $\Delta P$ is the pressure drop between the aorta and distal location, and $v_{rest}$ is the blood flow velocity, both under rest state conditions. Measured coronary pressure or velocity may be used similarly to what was described above for HSR in order to improve the estimation of the BSR index.

Enhancement of Blood Flow Computations for a Different Patient State or Different Quantity of Interest In another embodiment of the present invention, the method of FIG. 1 can be applied to enhance blood flow computations when the patient state at which the invasive physiological measurement is performed is different from the patient state for which the computational blood flow model is applied. For example, an invasive pressure measurement may be performed at rest, while the blood flow simulation may be performed for the hyperemic state. In this case, the invasive measurements performed at rest may be used to personalize and to adapt model parameters and boundary conditions for a blood flow simulation at the rest state. Then, only a subset of these parameters (specifically only the coronary microvascular resistances) must be modified in order to perform the blood flow simulation for the hyperemic state. In a possible implementation, only state-independent parameters (e.g., parameters that do not change for rest or hyperemia state) of the computational blood flow model may be personalized based on the rest-state invasive measurements. This approach has the advantage that it does not require the administration of a vasodilating drug for achieving hyperemia (which bears a certain risk of complications for the patient).

In another exemplary implementation, the invasive measurement may be performed for a pre-stenting state, whereas the blood flow computation may be performed for a post-stenting state to simulate the effect of stenting on one or more stenoses. In this case, the invasive measurements performed for the pre-stenting state are used to personalize and to adapt model parameters and boundary conditions for a blood flow simulation at the pre-stenting state. Then, only a subset of parameters of the computational blood flow model must be modified to perform the blood flow simulation for the post-stenting state. For example, the patient-specific anatomical model can be reconstructed to adapt the geometry of the stenosis region for which stenting is applied and the computational model adjusted based on the reconstructed patient-specific anatomical model. Alternatively, parameters of the stenosis pressure drop model can be directly adapted to represent the effect of the stenting, as described in United State Patent Publication No. 2015/0374243, entitled "Method and System for Prediction of Post-Stenting Hemodynamic Metrics for Treatment Planning of Arterial Stenosis", which is incorporated herein by reference in its entirety. This approach has the advantage that the pre-stenting measurement allows for a correct personalization of the model parameters and, as a result, the post-stenting hemodynamic computation may be able to correctly assess the success of the intervention.

Generation of an Indication for a Specific Patient Condition

Figure 8:
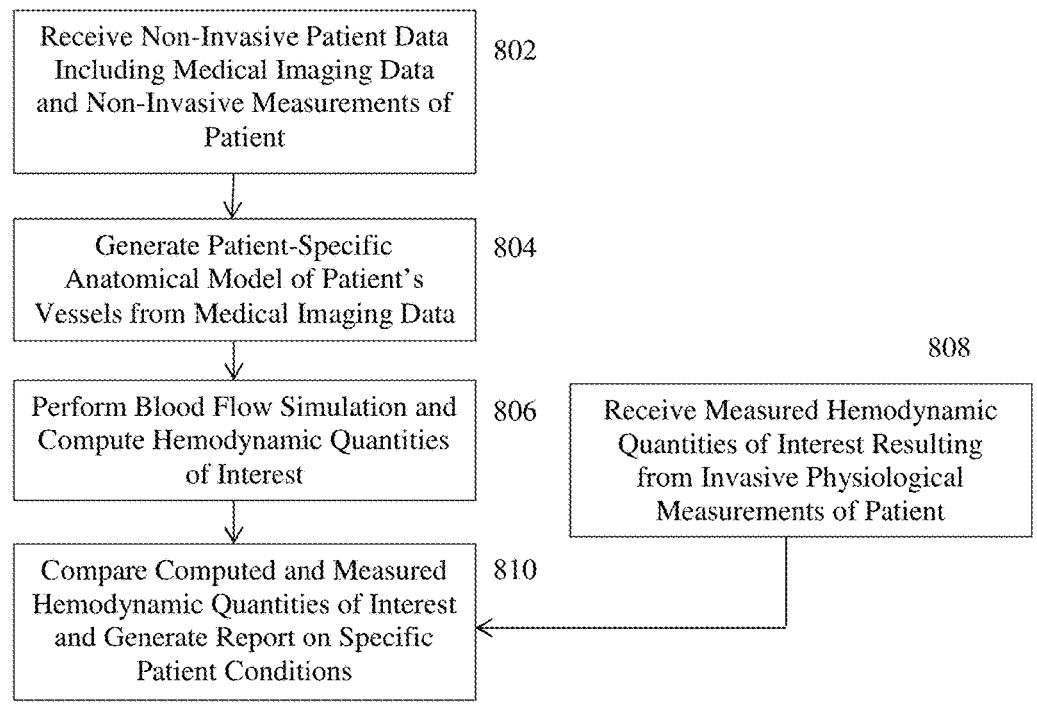
FIG. 8 illustrates a method for generating an indication of a specific patient condition according to an embodiment of the present invention.

In another embodiment of the present invention, a combination of computational blood flow modeling and invasive measurements may be used to generate an indication of a specific patient condition for a clinician. FIG. 8 illustrates a method for generating an indication of a specific patient condition according to an embodiment of the present invention. Steps 802 and 804 of the method of FIG. 8 are the same as steps 102 and 104 of FIG. 1, and can be implemented as described above in connection with FIG. 1. At step 806, a blood flow simulation is performed and hemodynamic quantities of interest are computed without taking into account any invasive measurements of the patient. In particular, a computational blood flow model, such as the computational blood flow model illustrated in FIG. 3, is generated based on the patient-specific anatomical model of the patient's vessel and parameters and boundary conditions for the computational blood flow model are determined based on the non-invasive patient data. The computational blood flow model computed blood flow and pressure values at a plurality of locations in the patient-specific anatomical model over a plurality of time steps. The computed blood flow and pressure values are used to compute hemodynamic quantities of interest. At step 808, measured hemodynamic quantities of interest resulting from invasive physiological measurements of the patient (e.g., pressure, flow rate, velocity, etc.) are received. At step 810, the computed and measured hemodynamic quantities of interest are compared and a report on specific patient conditions is generated based on the comparison. The report is output, for example, by displaying the report or indication on a display device of a computer system. The computed quantities of interest, which do not take into consideration the invasively measured quantities, are compared with the measured hemodynamic quantities of interest and if the difference is larger than a certain threshold value, a report on a specific condition is generated.

In an exemplary implementation, if the measured hyperemic coronary velocity is much smaller than the computed hyperemic coronary velocity (i.e., the difference is greater than a threshold value), this may be an indication of microvascular disease which limits the flow/velocity increase at hyperemia. In this case, a report or indication can be generated that alerts a clinician that the patient may have microvascular disease. In another exemplary implementation, if the measured coronary velocity is smaller than the computed coronary velocity ((i.e., the difference is greater than a threshold value) at both rest and hyperemia, this may be an indication of a recent myocardial infarction in the region subtended by the corresponding coronary vessel (due to tissue scarring at myocardial infarction, the amount of flow required by the corresponding tissue diminishes). In this case, a report or indication can be generated that alerts a clinician that the patient may have had a recent myocardial infarction. This report or indication may also provide the region where the myocardial infarction may have occurred.

Figure 9:
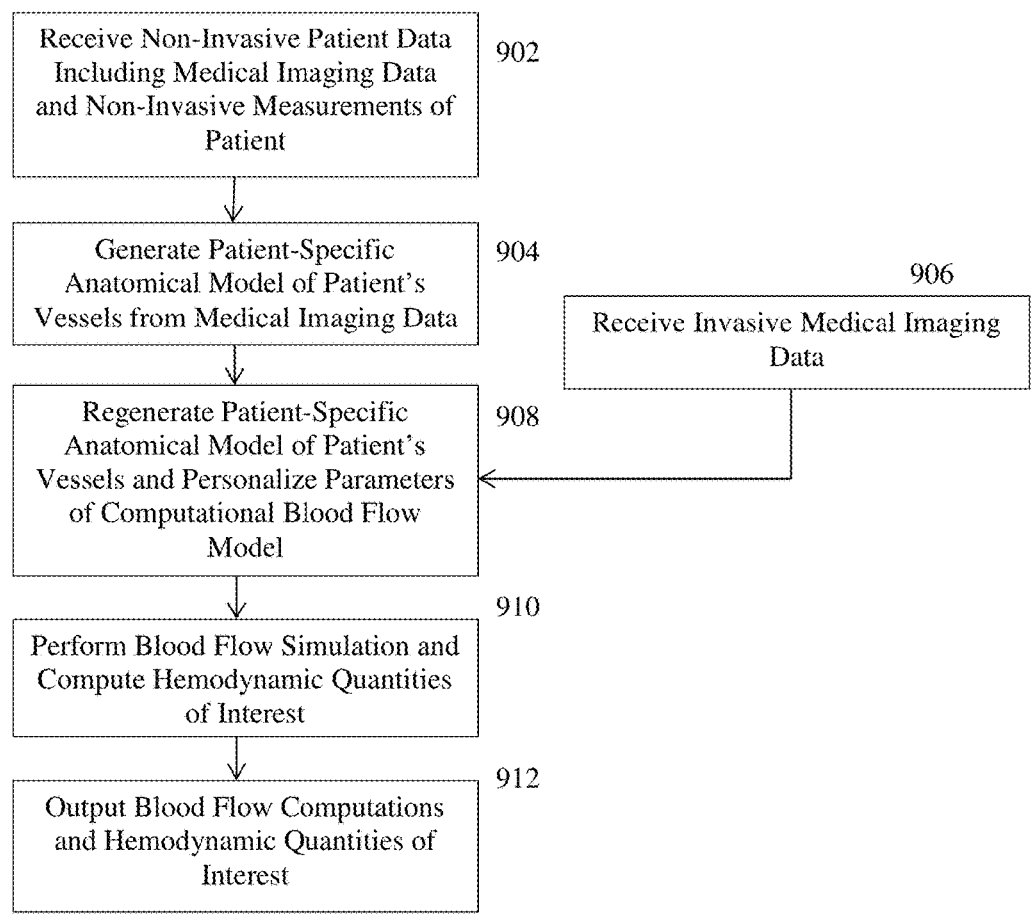
FIG. 9 illustrates a method for combining invasive and non-invasive medical imaging to enhance blood flow computation according to an embodiment of the present invention.

Combining Invasive and Non-Invasive Medical Imaging Techniques to Improve Blood Flow Computation Results In another embodiment of the present invention, the method of FIG. 1 is applied to combine invasive and non-invasive medical imaging techniques to improve blood flow computation results. FIG. 9 illustrates a method for combining invasive and non-invasive medical imaging to enhance blood flow computation according to an embodiment of the present invention. Steps 902 and 904 of the method of FIG. 9 are the same as steps 102 and 104 of FIG. 1, and can be implemented as described above in connection with FIG. 1. At step 906, invasive medical imaging data of the patient is received. For example, an invasive medical imaging technique, such as angiography or intravascular ultrasound (IVUS) can be used to acquire additional medical imaging data. Invasive medical imaging techniques typically have higher resolutions than non-invasive medical imaging techniques and may focus on specific regions of interest in the patient's vessels. At step 908, the patient-specific anatomical model of the patient's vessels is regenerated based on the invasive medical imaging data, and parameters of the computational model are personalized based on the regenerated patient-specific anatomical model. The used of additional invasive medical imaging data may enable the generation of a superior anatomical model of the patient's vessels. Invasive medical imaging techniques typically have higher resolutions than non-invasive techniques, but may allow for the reconstruction of only a sub-part of the patient-specific anatomical model. The invasive medical imaging may focus on specific regions of interest of the patient-specific anatomical model (e.g., stenoses), as identified in the non-invasively acquired medical images. An improved reconstruction of the patient-specific anatomical model resulting from the invasive medical imaging data may improve the personalization of the computational blood flow model and also the computational results of the blood flow model. At step 910, the blood flow simulation is performed and the hemodynamic quantities of interest are computed using the personalized computational blood flow model. At step 912, the blood flow computations and hemodynamic quantities of interest are output, for example, by being displayed on a display device of a computer system.

As discussed in the various embodiments described above, various invasive physiological measurements (e.g., pressure, flow rate, velocity, etc.) are acquired for a patient. In a possible implementation, in the case of coronary computations, such measurements may not only be performed at individual locations, but a pullback curve from the distal location to the ostium of the coronary tree may be recorded. This pullback curve contains information related to the locations where the pressure drop is most significant. This information may be used to parameterize the computational blood flow model along the path of the pullback.

In the case of coronary computations, invasive measurements may be performed in on coronary tree (e.g., LCA) and the personalized parameters (used for example when relating flow rate to the radius) determined from these measurements may be used in the blood flow computations performed for the other coronary tree (e.g. RCA).

Invasive measurements may be performed subsequently at different times (e.g., initial diagnosis and follow-up examination). The computational blood flow model personalization and hemodynamic computation (simulation) may be rerun after each of these invasive measurements becomes available.

Various embodiments described above for coronary computations may be applied for other parts of the cardiovascular system. For example, in the case of aortic coarctation, invasive measurements may be performed at rest, and by personalizing the parameters in the computational blood flow model to match these measurements, the blood flow computations for the exercise state may be enhanced.

For the use case of generating an indication for a specific patient condition, the computational blood flow model can be applied to answer "what-if" scenarios. The model parameters may be personalized by excluding and respectively including the invasive measurements. The magnitude and direction of the changes in the parameters between the two different personalization procedures may offer insights into the clinical state of the patient. For example, if in the new personalization (using the invasive measurements) the peripheral resistance decreases significantly, this may indicate microvascular disease.

Considering that two parameter personalization results, obtained by excluding and respectively including the invasive measurements, are available for a large number of patients, consistent differences between the personalization results may be used to improve the personalization procedure which does not use invasive measurements. Thus, consistent biases, as given for example by gender or age difference, that were not previously considered, may be accounted for.

Figure 10:
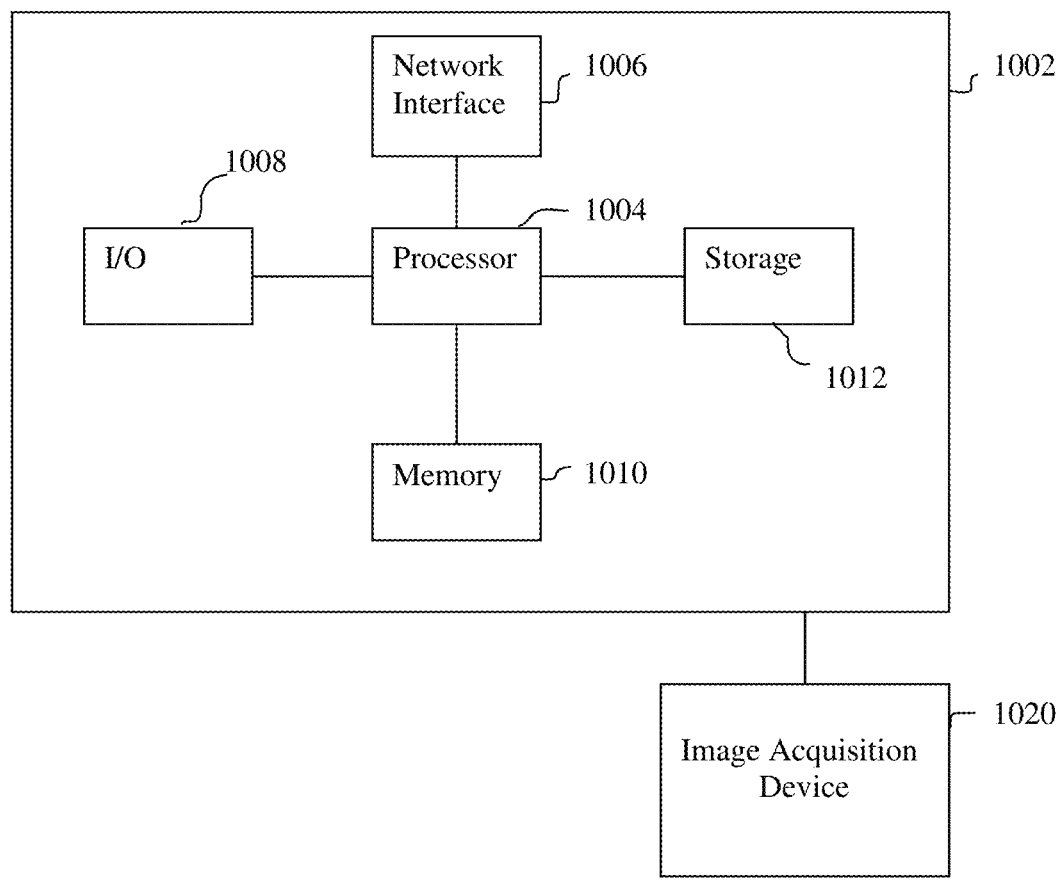
FIG. 10 is a high-level block diagram of a computer capable of implementing the present invention.

The above-described methods may be implemented on a computer using well-known computer processors, memory units, storage devices, computer software, and other components. A high-level block diagram of such a computer is illustrated in FIG. 10. Computer 1002 contains a processor 1004, which controls the overall operation of the computer 1002 by executing computer program instructions which define such operation. The computer program instructions may be stored in a storage device 1012 (e.g., magnetic disk) and loaded into memory 1010 when execution of the computer program instructions is desired. Thus, the steps of the methods of FIGS. 1, 4, 6, 8, and 9 may be defined by the computer program instructions stored in the memory 1010 and/or storage 1012 and controlled by the processor 1004 executing the computer program instructions. An image acquisition device 1020, such as a CT scanning device, MR scanning device, Ultrasound device, etc., can be connected to the computer 1002 to input image data to the computer 1002. It is possible to implement the image acquisition device 1020 and the computer 1002 as one device. It is also possible that the image acquisition device 1020 and the computer 1002 communicate wirelessly through a network. In a possible embodiment, the computer 1002 may be located remotely with respect to the image acquisition device 1020 and the method steps are performed as part of a server or cloud based service. The computer 1002 also includes one or more network interfaces 1006 for communicating with other devices via a network. The computer 1002 also includes other input/output devices 1008 that enable user interaction with the computer 1002 (e.g., display, keyboard, mouse, speakers, buttons, etc.). Such input/output devices 1008 may be used in conjunction with a set of computer programs as an annotation tool to annotate medical image data received from the image acquisition device 1020. One skilled in the art will recognize that an implementation of an actual computer could contain other components as well, and that FIG. 10 is a high level representation of some of the components of such a computer for illustrative purposes.

The above-described methods may be implemented using computers operating in a client-server relationship. Typically, in such a system, the client computers are located remotely from the server computer and interact via a network. The client-server relationship may be defined and controlled by computer programs running on the respective client and server computers.

The above-described methods may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 1, 4, 6, 8, and 9. Certain steps of the methods described herein, including one or more of the steps of FIGS. 1, 4, 6, 8, and 9, may be performed by a server or by another processor in a network-based cloud-computing system. Certain steps of the methods described herein, including one or more of the steps of FIGS. 1, 4, 6, 8, and 9, may be performed by a client computer in a network-based cloud computing system. The steps of the methods described herein, including one or more of the steps of FIGS. 1, 4, 6, 8, and 9, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for simulating blood flow in a vessel of a patient to estimate one or more hemodynamic quantities of interest, comprising:
    receiving non-invasive patient data including medical image data and non-invasive clinical measurements of a patient;
    generating a patient-specific anatomical model of at least one vessel of the patient from the medical image data;
    receiving an invasive physiological measurement of the patient acquired using a sensor inserted into a particular vessel of the patient at a first patient state;
    personalizing a computational blood flow model for simulating blood flow in the patient-specific anatomical model of the at least one vessel of the patient by reconstructing the patient-specific anatomical model based on the invasive physiological measurement of the patient and personalizing one or more parameters or boundary conditions of the computational blood flow model based on the reconstructed patient-specific anatomical model; and
    simulating blood flow in the patient-specific anatomical model of the at least one vessel of the patient at a second patient state and computing one or more hemodynamic quantities of interest using the personalized computational blood flow model.

2. The method of claim 1, wherein the invasive physiological measurement is a different quantity than the one or more hemodynamic quantities of interest computed using the personalized computational blood flow model.

3. The method of claim 1, wherein the particular vessel from which the invasive physiological measurement of the patient is acquired is different that the at least one vessel of the patient for which the blood flow is simulated using the personalized computational blood flow model.

4. The method of claim 1, wherein:
    receiving an invasive physiological measurement of the patient acquired using a sensor inserted into a particular vessel of the patient at a first patient state comprises receiving invasive measurements of an aortic pressure and a distal pressure for a stenosis in the at least one vessel;
    personalizing a computational blood flow model comprises:
        calculating an invasively measured pressure drop for the stenosis from the invasive aortic and distal pressure measurements, and
        adjusting a flow rate through the stenosis in the computational blood flow model to determine a flow rate for which a simulated pressure drop for the stenosis computed using the computational blood flow model matches the invasively measured pressure drop for the stenosis; and
    simulating blood flow in the patient-specific anatomical model of the at least one vessel of the patient at a second patient state and computing one or more hemodynamic quantities of interest using the personalized computational blood flow model comprises:
        computing a transit time based on the determined flow rate and computing an index of microvascular resistance (IMR) based on the transit time and the distal pressure measurement.

5. The method of claim 4, wherein simulating blood flow in the patient-specific anatomical model of the at least one vessel of the patient at a second patient state and computing one or more hemodynamic quantities of interest using the personalized computational blood flow model further comprises:
    computing a microvascular resistance based on the determined flow rate and the distal pressure measurement.

6. The method of claim 1, wherein:
    receiving an invasive physiological measurement of the patient acquired using a sensor inserted into a particular vessel of the patient at a first patient state comprises receiving an invasive blood velocity measurement for the at least one vessel of the patient;
    personalizing a computational blood flow model comprises calculating a flow rate for the computational blood flow model based on the invasive flow velocity measurement and a cross-sectional area in the patient-specific anatomical model of the at least one vessel; and simulating blood flow in the patient-specific anatomical model of the at least one vessel of the patient at a second patient state and computing one or more hemodynamic quantities of interest using the personalized computational blood flow model comprises:

simulating blood flow in the patient-specific anatomical model of the at least one vessel with the calculated flow rate imposed in the computational blood flow model, computing a pressure drop over a stenosis in the at least one vessel based on the simulated blood flow, determining a distal pressure to the stenosis based on the computed pressure drop and an average aortic pressure estimated from non-invasive pressure measurements of the patient, computing a microvascular resistance based on the distal pressure and the simulated blood flow through the stenosis, and computing a transit time based on the simulated flow rate and computing an index of microvascular resistance (IMR) based on the transit time and the distal pressure.

7. The method of claim 1, wherein:

receiving an invasive physiological measurement of the patient acquired using a sensor inserted into a particular vessel of the patient at a first patient state comprises receiving an invasive measurement of a transit time required for blood to pass a stenosis region in the at least one vessel of the patient;

personalizing a computational blood flow model comprises calculating a flow rate through the stenosis region for the computational blood flow model based on the invasive measurement of the transit time and a volume of the stenosis region in the patient-specific anatomical model of the at least one vessel; and simulating blood flow in the patient-specific anatomical model of the at least one vessel of the patient at a second patient state and computing one or more hemodynamic quantities of interest using the personalized computational blood flow model comprises:

simulating blood flow in the patient-specific anatomical model of the at least one vessel with the calculated flow rate through the stenosis region imposed in the computational blood flow model, computing a pressure drop over the stenosis region in the at least one vessel based on the simulated blood flow, determining a distal pressure to the stenosis region based on the computed pressure drop and an average aortic pressure estimated from non-invasive pressure measurements of the patient, computing a microvascular resistance based on the distal pressure and the calculated flow rate through the stenosis region, and computing an index of microvascular resistance (IMR) based on the transit time and the distal pressure.

8. The method of claim 1, wherein:

receiving an invasive physiological measurement of the patient acquired using a sensor inserted into a particular vessle of the patient at a first patient state comprises receiving invasive pressure measurements of an aortic pressure and a distal pressure for a stenosis in the at least one vessel;

personalizing a computational blood flow model comprises:

calculating an invasively measured pressure drop for the stenosis from the invasive aortic and distal pressure measurements, and adjusting a flow rate through the stenosis in the computational blood flow model to determine a flow rate for which a simulated pressure drop for the stenosis computed using the computational blood flow model matches the invasively measured pressure drop for the stenosis; and simulating blood flow in the patient-specific anatomical model of the at least one vessel of the patient at a second patient state and computing one or more hemodynamic quantities of interest using the personalized computational blood flow model comprises:

simulating blood flow through the stenosis in the patient-specific anatomical model and computing a fractional flow reserve (FFR) and a coronary flow reserve (CFR) using the personalized computational blood flow model.

9. The method of claim 1, wherein:

receiving an invasive physiological measurement of the patient acquired using a sensor inserted into a particular vessel of the patient at a first patient state comprises receiving an invasive blood velocity measurement for the at least one vessel of the patient;

personalizing a computational blood flow model comprises calculating a flow rate for the computational blood flow model based on the invasive blood velocity measurement and a cross-sectional area in the patient-specific anatomical model of the at least one vessel; and simulating blood flow in the patient-specific anatomical model of the at least one vessel of the patient at a second patient state and computing one or more hemodynamic quantities of interest using the personalized computational blood flow model comprises:

simulating blood flow through the stenosis in the patient-specific anatomical model and computing a fractional flow reserve (FFR) and a coronary flow reserve (CFR) using the personalized computational blood flow model.

10. The method of claim 1, wherein the at least one vessel of the patient includes a plurality of stenosis regions and receiving an invasive physiological measurement of the patient acquired using a sensor inserted into a particular vessel of the patient at a first patient state comprises:

receiving an invasive aortic pressure measurement and an invasive distal pressure measurement measured at a location distal to a first one of the plurality of stenosis regions.

11. The method of claim 10, wherein personalizing a computational blood flow model comprises:

personalizing the computational blood flow model based on the invasive aortic pressure measurement and invasive distal pressure measurement measured at a location distal to the first one of the plurality of stenosis regions.

12. The method of claim 11, wherein simulating blood flow in the patient-specific anatomical model of the at least one vessel of the patient at a second patient state and computing one or more hemodynamic quantities of interest using the personalized computational blood flow model comprises:

simulating blood flow and pressure in the patient-specific anatomical model of the at least one of the at least one vessel of the patient fractional flow reserve (FFR) for each of the plurality of stenosis regions at a respective location distal to each of the plurality of stenosis regions using the personalized computational blood flow model.

13. The method of claim 12, wherein personalizing the computational blood flow model based on the invasive aortic pressure measurement and invasive distal pressure measurement measured at a location distal to the first one of the plurality of stenosis regions comprises:
adapting at least one of a flow rate, a pressure-based inlet boundary condition, parameters of stenosis pressure-drop models, or outlet boundary conditions of the computational blood flow model such that a computed pressure drop between a location at which the aortic pressure was measured and the location distal to the first one of the plurality of stenosis regions matches a measured pressure drop between the invasive aortic pressure measurement and the invasive distal pressure measurement.

14. The method of claim 1, wherein the first patient state is a rest state of the patient, the second patient state is a hyperemic state of the patient, and personalizing a computational blood flow model comprises:
personalizing one or more first parameters of the computational blood flow model for a blood flow simulation at the rest state based on the invasive physiological measurement acquired at the rest state; and
modifying at least one second parameter of the computational blood flow model to perform the blood flow simulation at the hyperemic state.

15. The method of claim 1, wherein the first patient state is a pre-stenting state of the patient, the second patient state is a post-stenting state of the patient, and personalizing a computational blood flow model comprises:
personalizing the computational blood flow model for a blood flow simulation at the pre-stenting state based on the invasive physiological measurement acquired at the pre-stenting state; and
modifying at least one parameter of the personalized computational blood flow model to perform the blood flow simulation for the post-stenting state.

16. The method of claim 1, wherein the invasive physiological measurement of the patient comprises invasive medical imaging data of at least a portion of the at least one vessel of the patient, and wherein reconstructing the patient-specific anatomical model based on the invasive physiological measurement of the patient comprises:
reconstructing the patient-specific anatomical model of the at least one vessel based on the invasive medical imaging data.

17. A method for generating an indication of a specific patient condition based on blood flow computations and invasive physiological measurements, comprising:
receiving non-invasive patient data including medical image data and non-invasive clinical measurements of a patient;
generating a patient-specific anatomical model of at least one vessel of the patient from the medical image data;
simulating blood flow in the patient-specific anatomical model of the at least one vessel of the patient at a second patient state and computing at least one hemodynamic quantity of interest using a computational blood flow model, the computational blood flow model personalized by:
reconstructing the patient-specific anatomical model based on an invasive physiological measurement of the paient acquired using a sensor inserted into a particular vessel of the patient at a first patient state, and
personalizing one or more parameters or boundary conditions of the computational blood flow model based on the reconstructed patient-specific anatomical model;
receiving at least one measured hemodynamic quantity of interest resulting from the invasive physiological measurements of the patient;
comparing the at least one computed hemodynamic quantity of interest with the at least one measured hemodynamic quantity of interest; and
generating an indication of specific patient condition in response to a difference between the at least one computed hemodynamic quantity of interest and the at least one measured hemodynamic quantity of interest being greater than a threshold value.

18. The method of claim 17, wherein the at least one computed hemodynamic quantity of interest comprises a computed hyperemic coronary velocity, the at least one measured hemodynamic quantity of interest comprises a measured hyperemic coronary velocity, and generating an indication of specific patient condition in response to a difference between the at least one computed hemodynamic quantity of interest and the at least one measured hemodynamic quantity of interest being greater than a threshold value comprises:
generating an indication of microvascular disease in response to a determination that the measured hyperemic coronary velocity is smaller than the computed hyperemic coronary velocity by more than the threshold value.

19. The method of claim 17, wherein the at least one computed hemodynamic quantity of interest comprises a computed coronary blood velocity at rest and a computed coronary blood velocity at hyperemia, the at least one measured hemodynamic quantity of interest comprises a measured coronary blood velocity at rest and a measured coronary blood velocity at hyperemia, and generating an indication of specific patient condition in response to a difference between the at least one computed hemodynamic quantity of interest and the at least one measured hemodynamic quantity of interest being greater than a threshold value comprises:
generating an indication of a recent myocardial infarction in response to a determination that the measured coronary velocity at rest is smaller than the computed hyperemic coronary velocity at rest by more than the threshold value and the measured coronary velocity at hyperemia is smaller than the computed hyperemic coronary velocity at hyperemia by more than the threshold value.

20. An apparatus for simulating blood flow in a vessel of a patient to estimate one or more hemodynamic quantities of interest, comprising:
a processor; and
a memory storing computer program instructions which when executed by the processor cause the processor to perform operations comprising:
receiving non-invasive patient data including medical image data and non-invasive clinical measurements of a patient;
generating a patient-specific anatomical model of at least one vessel of the patient from the medical image data;
receiving an invasive physiological measurement of the patient acquired using a sensor inserted into a particular vessel of the patient at a first patient state;

personalizing a computational blood flow model for simulating blood flow in the patient-specific anatomical model of the at least one vessel of the patient by reconstructing the patient-specific anatomical model based on the invasive physiological measurement of the patient and personalizing one or more parameters or boundary conditions of the computational blood flow model based on the reconstructed patient-specific anatomical model; and simulating blood flow in the patient-specific anatomical model of the at least one vessel of the patient at a second patient stateand computing one or more hemodynamic quantities of interest using the personalized computational blood flow model.

21. The apparatus of claim 20, wherein:

receiving an invasive physiological measurement of the patient acquired using a sensor inserted into a particular vessel of the patient at a first patient state comprises receiving invasive pressure measurements of an aortic pressure and a distal pressure for a stenosis in the at least one vessel;

personalizing a computational blood flow model comprises:
  calculating an invasively measured pressure drop for the stenosis from the invasive aortic and distal pressure measurements, and
  adjusting a flow rate through the stenosis in the computational blood flow model to determine a flow rate for which a simulated pressure drop for the stenosis computed using the computational blood flow model matches the invasively measured pressure drop for the stenosis; and simulating blood flow in the patient-specific anatomical model of the at least one vessel of the patient at a second patient state and computing one or more hemodynamic quantities of interest using the personalized computational blood flow model comprises:
  computing a microvascular resistance based on the determined flow rate and the distal pressure measurement, and
  computing a transit time based on the determined flow rate and computing an index of microvascular resistance (IMR) based on the transit time and the distal pressure measurement.

22. The apparatus of claim 20, wherein:

receiving an invasive physiological measurement of the patient acquired using a sensor inserted into a particular vessel of the patient at a first patient state comprises receiving an invasive flow velocity measurement for the at least one vessel of the patient;

personalizing a computational blood flow model comprises calculating a flow rate for the computational blood flow model based on the invasive flow velocity measurement and a cross-sectional area in the patient-specific anatomical model of the at least one vessel; and simulating blood flow in the patient-specific anatomical model of the at least one vessel of the patient at a second patient side and computing one or more hemodynamic quantities of interest using the personalized computational blood flow model comprises:
  simulating blood flow in the patient-specific anatomical model of the at least one vessel with the calculated flow rate imposed in the computational blood flow model,
  computing a pressure drop over a stenosis in the at least one vessel based on the simulated blood flow,
  determining a distal pressure to the stenosis based on the computed pressure drop and an average aortic pressure estimated from non-invasive pressure measurements of the patient,
  computing a microvascular resistance based on the distal pressure and the simulated flow rate through the stenosis, and
  computing a transit time based on the simulated flow rate and computing an index of microvascular resistance (IMR) based on the transit time and the distal pressure.

23. The apparatus of claim 20, wherein:

receiving an invasive physiological measurement of the patient acquired using a sensor inserted into a particular vessel of the patient at a first patient state comprises receiving an invasive measurement of a transit time required for blood to pass a stenosis region in the at least one vessel of the patient;

personalizing a computational blood flow model comprises calculating a flow rate through the stenosis region for the computational blood flow model based on the invasive measurement of the transit time and a volume of the stenosis region in the patient-specific anatomical model of the at least one vessel; and simulating blood flow in the patient-specific anatomical model of the at least one vessel of the patient at a second patient state and computing one or more hemodynamic quantities of interest using the personalized computational blood flow model comprises:
  simulating blood flow in the patient-specific anatomical model of the at least one vessel with the calculated flow rate through the stenosis region imposed in the computational blood flow model,
  computing a pressure drop over the stenosis region in the at least one vessel based on the simulated blood flow,
  determining a distal pressure to the stenosis region based on the computed pressure drop and an average aortic pressure estimated from non-invasive pressure measurements of the patient,
  computing a microvascular resistance based on the distal pressure and the calculated flow rate through the stenosis region, and
  computing an index of microvascular resistance (IMR) based on the transit time and the distal pressure.

24. The apparatus of claim 20, wherein:

receiving an invasive physiological measurement of the patient acquired using a sensor inserted into a particular vessel of the patient at a first patient state comprises receiving invasive pressure measurements of an aortic pressure and a distal pressure for a stenosis in the at least one vessel;

personalizing a computational blood flow model comprises:
  calculating an invasively measured pressure drop for the stenosis from the invasive aortic and distal pressure measurements, and
  adjusting a flow rate through the stenosis in the computational blood flow model to determine a flow rate for which a simulated pressure drop for the stenosis computed using the computational blood flow model matches the invasively measured pressure drop for the stenosis; and simulating blood flow in the patient-specific anatomical model of the at least one vessel of the patient at a second patient state and computing one or more hemodynamic quantities of interest using the personalized computational blood flow model comprises:
simulating blood flow through the stenosis in the patient-specific anatomical model and computing a fractional flow reserve (FFR) and a coronary flow reserve (CFR) using the personalized computational blood flow model.

25. The apparatus of claim 20, wherein:
receiving an invasive physiological measurement of the patient acquired using a sensor inserted into a particular vessel of the patient at a first patient state comprises receiving an invasive flow velocity measurement for the at least one vessel of the patient;
personalizing a computational blood flow model comprises calculating a flow rate for the computational blood flow model based on the invasive flow velocity measurement and a cross-sectional area in the patient-specific anatomical model of the at least one vessel; and
simulating blood flow in the patient-specific anatomical model of the at least one vessel of the patient at a second patient state and computing one or more hemodynamic quantities of interest using the personalized computational blood flow model comprises:
simulating blood flow through the stenosis in the patient-specific anatomical model and computing a fractional flow reserve (FFR) and a coronary flow reserve (CFR) using the personalized computational blood flow model.

26. The apparatus of claim 20, wherein the at least one vessel of the patient includes a plurality of stenosis regions and receiving an invasive physiological measurement of the patient acquired using a sensor inserted into a particular vessel of the patient at a first patient state comprises:
receiving an invasive aortic pressure measurement and an invasive distal pressure measurement measured at a location distal to a first one of the plurality of stenosis regions.

27. The apparatus of claim 26, wherein:
personalizing a computational blood flow model comprises:
personalizing the computational blood flow model the invasive aortic pressure measurement and invasive distal pressure measurement measured at a location distal to the first one of the plurality of stenosis regions; and
simulating blood flow in the patient-specific anatomical model of the at least one vessel of the patient at a second patient state and computing one or more hemodynamic quantities of interest using the personalized computational blood flow model comprises:
simulating blood flow and pressure in the patient-specific anatomical of the at least one of the at least one vessel of the patient and computing fractional flow reserve (FFR) for each of the plurality of stenosis regions at a respective location distal to each of the plurality of stenosis regions using the personalized computational blood flow model.

28. The apparatus of claim 20, wherein the first patient state is a rest state of the patient, the second patient state is a hyperemic state of the patient, and personalizing a computational blood flow model comprises:
personalizing one or more first parameters of the computational blood flow model for a blood flow simulation at the rest state based on the invasive physiological measurement acquired at the rest state; and
modifying at least one second parameter of the computational blood flow model to perform the blood flow simulation at the hyperemic state.

29. The apparatus of claim 20, wherein the first patient state is a pre-stenting state of the patient, the second patient state is a post-stenting state of the patient, and personalizing a computational blood flow model comprises:
personalizing the computational blood flow model for a blood flow simulation at the pre-stenting state based on the invasive physiological measurement acquired at the pre-stenting state; and
modifying at least parameter of the personalized computational blood flow model to perform the blood flow simulation for the post-stenting state.

30. The apparatus of claim 20, wherein the invasive physiological measurement of the patient comprises the invasive medical imaging data of at least a portion of the at least one vessel of the patient, and wherein reconstructing the patient-specific anatomical model based on the invasive physiological measurement of the patient comprises:
reconstructing the patient-specific anatomical model of the at least one vessel based on the invasive medical imaging data.

31. A non-transitory computer readable medium storing computer program instructions for simulating blood flow in a vessel of a patient to estimate one or more hemodynamic quantities of interest, the computer program instructions when execute by a processor cause the processor to perform operations comprising:
receiving non-invasive patient data including medical image data and non-invasive clinical measurements of a patient;
generating a patient-specific anatomical model of at least one vessel of the patient from the medical image data;
receiving an invasive physiological measurement of the patient acquired using a sensor inserted into a particular vessel of the patient at a first patient state;
personalizing a computational blood flow model for simulating blood flow in the patient-specific anatomical model of the at least one vessel of the patient by reconstructing the patient-specific anatomical model based on the invasive physiological measurement of the patient and personalizing one or more parameters or boundary conditions of the computational blood flow model based on the reconstructed patient-specific anatomical model; and
simulating blood flow in the patient-specific anatomical model of the at least one vessel of the patient at a second patient state and computing one or more hemodynamic quantities of interest using the personalized computational blood flow model.

32. The non-transitory computer readable medium of claim 31, wherein:
receiving an invasive physiological measurement of the patient acquired using a sensor inserted into a particular vessel of the patient at a first patient state comprises receiving invasive pressure measurements of an aortic pressure and a distal pressure for a stenosis in the at least one vessel;
personalizing a computational blood flow model comprises:
calculating an invasively measured pressure drop for the stenosis from the invasive aortic and distal pressure measurements, and
adjusting a flow rate through the stenosis in the computational blood flow model to determine a flow rate for which a simulated pressure drop for the stenosis computed using the computational blood flow model matches the invasively measured pressure drop for the stenosis; and simulating blood flow in the patient-specific anatomical model of the at least one vessel of the patient and computing one or more hemodynamic quantities of interest using the personalized computational blood flow model comprises:
- computing a microvascular resistance based on the determined flow rate and the distal pressure measurement, and
- computing a transit time based on the determined flow rate and computing an index of microvascular resistance (IMR) based on the transit time and the distal pressure measurement.

33. The non-transitory computer readable medium of claim 31, wherein:

receiving an invasive physiological measurement of the patient acquired using a sensor inserted into a particular vessel of the patient at a first patient state comprises receiving an invasive flow velocity measurement for the at least one vessel of the patient;

personalizing a computational blood flow model comprises calculating a flow rate for the computational blood flow model based on the invasive flow velocity measurement and a cross-sectional area in the patient-specific anatomical model of the at least one vessel; and simulating blood flow in the patient-specific anatomical model of the at least one vessel of the patient at a second patient state and computing one or more hemodynamic quantities of interest using the personalized computational blood flow model comprises:
- simulating blood flow in the patient-specific anatomical model of the at least one vessel with the calculated flow rate imposed in the computational blood flow model,
- computing a pressure drop over a stenosis in the at least one vessel based on the simulated blood flow,
- determining a distal pressure to the stenosis based on the computed pressure drop and an average aortic pressure estimated from non-invasive pressure measurements of the patient,
- computing a microvascular resistance based on the distal pressure and the simulated flow rate through the stenosis, and
- computing a transit time based on the simulated flow rate and computing an index of microvascular resistance (IMR) based on the transit time and the distal pressure.

34. The non-transitory computer readable medium of claim 31, wherein:

receiving an invasive physiological measurement of the patient acquired using a sensor inserted into a particular vessel of the patient at a first patient state comprises receiving an invasive measurement of a transit time required for blood to pass a stenosis region in the at least one vessel of the patient;

personalizing a computational blood flow model comprises calculating a flow rate through the stenosis region for the computational blood flow model based on the invasive measurement of the transit time and a volume of the stenosis region in the patient-specific anatomical model of the at least one vessel; and simulating blood flow in the patient-specific anatomical model of the at least one vessel of the patient at a second patient state and computing one or more hemodynamic quantities of interest using the personalized computational blood flow model comprises:
- simulating blood flow in the patient-specific anatomical model of the at least one vessel with the calculated flow rate through the stenosis region imposed in the computational blood flow model,
- computing a pressure drop over the stenosis region in the at least one vessel based on the simulated blood flow,
- determining a distal pressure to the stenosis region based on the computed pressure drop and an average aortic pressure estimated from non-invasive pressure measurements of the patient,
- computing a microvascular resistance based on the distal pressure and the calculated flow rate through the stenosis region, and
- computing an index of microvascular resistance (IMR) based on the transit time and the distal pressure.

35. The non-transitory computer readable medium of claim 31, wherein:

receiving an invasive physiological measurement of the patient acquired using a sensor inserted into a particular vessel of the patient at a first patient state comprises receiving invasive pressure measurements of an aortic pressure and a distal pressure for a stenosis in the at least one vessel;

personalizing a computational blood flow model comprises:
- calculating an invasively measured pressure drop for the stenosis from the invasive aortic and distal pressure measurements, and
- adjusting a flow rate through the stenosis in the computational blood flow model to determine a flow rate for which a simulated pressure drop for the stenosis computed using the computational blood flow model matches the invasively measured pressure drop for the stenosis; and simulating blood flow in the patient-specific anatomical model of the at least one vessel of the patient at a second patient state and computing one or more hemodynamic quantities of interest using the personalized computational blood flow model comprises:
- simulating blood flow through the stenosis in the patient-specific anatomical model and computing a fractional flow reserve (FFR) and a coronary flow reserve (CFR) using the personalized computational blood flow model.

36. The non-transitory computer readable medium of claim 31, wherein:

receiving an invasive physiological measurement of the patient acquired using a sensor inserted into a particular vessel of the patient at a first patient state comprises receiving an invasive flow velocity measurement for the at least one vessel of the patient;

personalizing a computational blood flow model comprises calculating a flow rate for the computational blood flow model based on the invasive flow velocity measurement and a cross-sectional area in the patient-specific anatomical model of the at least one vessel; and simulating blood flow in the patient-specific anatomical model of the at least one vessel of the patient at a second patient state and computing one or more hemodynamic quantities of interest using the personalized computational blood flow model comprises:
- simulating blood flow through the stenosis in the patient-specific anatomical model and computing a fractional flow reserve (FFR) and a coronary flow reserve (CFR) using the personalized computational blood flow model.

37. The non-transitory computer readable medium of claim 31, wherein the at least one vessel of the patient includes a plurality of stenosis regions and receiving an invasive physiological measurement of the patient acquired using a sensor inserted into a particular vessel of the patient at a first patient state comprises:

receiving an invasive aortic pressure measurement and an invasive distal pressure measurement measured at a location distal to a first one of the plurality of stenosis regions.

38. The non-transitory computer readable medium of claim 37, wherein:

personalizing a computational blood flow model comprises:

personalizing the computational blood flow model the invasive aortic pressure measurement and invasive distal pressure measurement measured at a location distal to the first one of the plurality of stenosis regions; and simulating blood flow in the patient-specific anatomical model of the at least one vessel of the patient at a second patient state and computing one or more hemodynamic quantities of interest using the personalized computational blood flow model comprises:

simulating blood flow and pressure in the patient-specific anatomical of the at least one of the at least one vessel of the patient and computing fractional flow reserve (FFR) for each of the plurality of stenosis regions at a respective location distal to each of the plurality of stenosis regions using the personalized computational blood flow model.

39. The non-transitory computer readable medium of claim 31, wherein the first patient state is a rest state of the patient, the second patient state is a hyperemic state of the patient, and personalizing a computational blood flow model comprises:

personalizing one or more first parameters of the computational blood flow model for a blood flow simulation at the rest state based on the invasive physiological measurement acquired at the rest state; and modifying at least one second parameter of the computational blood flow model to perform the blood flow simulation at the hyperemic state.

40. The non-transitory computer readable medium of claim 31, wherein the first patient state is a pre-stenting state of the patient, the second patient state is a post-stenting state of the patient, and personalizing a computational blood flow model comprises:

personalizing the computational blood flow model for a blood flow simulation at the pre-stenting state based on the invasive physiological measurement acquired at the pre-stenting state; and modifying at least parameter of the personalized computational blood flow model to perform the blood flow simulation for the post-stenting state.

41. The non-transitory computer readable medium of claim 31, wherein the invasive physiological measurement of the patient comprises invasive medical imaging data of at least a portion of the at least one vessel of the patient and wherein reconstructing the patient-specific anatomical model based on the invasive physiological measurement of the patient comprises:

reconstructing the patient-specific anatomical model of the at least one vessel based on the invasive medical imaging data.

42. The method of claim 1, wherein the particular vessel from which the invasive physiological measurement of the patient is acquired is the same as the at least one vessel of the patient for which the blood flow is simulated using the personalized computational blood flow model.

43. The method of claim 17, wherein the particular vessel from which the invasive physiological measurements of the patient are acquired is the same as the at leat one vessel of the patient for which the blood flow is simulated using the computational blood flow model.

44. The method of claim 17, wherein the particular vessel from which the invasive physiological measurement of the patient are acquired is different than the at least one vessel of the patient for which the blood flow is simulated using the computational blood flow model.

45. The apparatus of claim 20, wherein the particular vessel from which the invasive physiological measurement of the patient is acquired is the same as the at least one vessel of the patient for which the blood flow is simulated using the personalized computational blood flow model.

46. The apparatus of claim 20, wherein the particular vessel from which the invasive physiological measurement of the patient is acquired is different than the at least one vessel of the patient for which the blood flow is simulated using the personalized computational blood flow model.

47. The non-transitory computer readable medium of claim 31, wherein the particular vessel from which the invasive physiological measurement of the patient is acquired is the same as the at least one vessel of the patient for which the blood flow is simulated using the personalized computational blood flow model.

48. The non-tramsitory computer readable medium of claim 31, wherein the particular vessel from which the invasive physiological measurement of the patient is acquired is different than the at least one vessel of the patient for which the blood flow is simulated using the personalized computational blood flow model.

* * * * *